(12) United States Patent
Lezec et al.

(10) Patent No.: US 6,770,867 B2
(45) Date of Patent: Aug. 3, 2004

(54) METHOD AND APPARATUS FOR SCANNED INSTRUMENT CALIBRATION

(75) Inventors: Henri J. Lezec, Strasbourg (FR); Christian R. Musil, Cambridge, MA (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 10/186,206

(22) Filed: Jun. 27, 2002

(65) Prior Publication Data

US 2003/0085352 A1 May 8, 2003

Related U.S. Application Data

(60) Provisional application No. 60/302,142, filed on Jun. 29, 2001.

(51) Int. Cl.[7] .............................................. H01J 37/28
(52) U.S. Cl. ........................ 250/252.1; 28/250; 28/31; 28/311; 28/307; 28/491.1; 28/364; 28/571.02; 28/310; 28/316; 28/317; 28/73; 28/105
(58) Field of Search ...................... 250/252.1, 310–311, 250/307, 491.1; 364/571.02; 310/316–317; 73/105

(56) References Cited

U.S. PATENT DOCUMENTS

| | | | |
|---|---|---|---|
| 3,876,883 A | 4/1975 | Broers et al. | 250/492 |
| 4,095,112 A | 6/1978 | Trotel | 250/492 A |
| 4,370,554 A | 1/1983 | Bohlen et al. | 250/491.1 |
| 4,379,230 A | 4/1983 | Bouwhuis et al. | 250/307 |
| 4,386,850 A * | 6/1983 | Leahy | 356/243.4 |
| 4,442,361 A | 4/1984 | Zasio et al. | 250/491.1 |
| 4,443,703 A | 4/1984 | Shimazu et al. | 250/491.1 |
| 4,763,004 A | 8/1988 | Yasuda et al. | 250/396 R |
| 5,644,512 A | 7/1997 | Chernoff et al. | 364/571.02 |
| 5,763,894 A | 6/1998 | Enichen et al. | 250/492.2 |
| 5,825,670 A * | 10/1998 | Chernoff et al. | 702/85 |
| 5,851,413 A | 12/1998 | Casella et al. | 216/92 |
| 5,960,255 A | 9/1999 | Bartha et al. | 438/14 |
| 6,194,718 B1 | 2/2001 | Dotan | 250/310 |

OTHER PUBLICATIONS

Nara et al. "Inspection Method, Apparatus and System for Circuit Pattern", Pub No: US 2002/0109088 A1, Aug. 15, 2002.*

* cited by examiner

Primary Examiner—John R. Lee
Assistant Examiner—Zia R. Hashmi
(74) Attorney, Agent, or Firm—Patrick Stellitano; Michael O. Scheinberg

(57) ABSTRACT

Methods and apparatus for calibration of a scanned beam system are provided by sampling a calibration specimen containing an array of targets with a spacing between samples that is greater than the spacing between targets in the array and forming an image from the samples to reduce calibration specimen degradation and to magnify calibration errors to enable very fine calibration of the scanned beam system.

45 Claims, 28 Drawing Sheets

METHOD AND APPARATUS FOR SCANNED INSTRUMENT CALIBRATION

This application claims priority from U.S. Provisional Patent Application No. 60/302,142, filed Jun. 29, 2001, which is hereby incorporated by reference.

TECHNICAL FIELD OF THE INVENTION

The present invention relates to the field of scanned beam microscopy, and in particular, to a method and apparatus for calibration of a scanned beam system.

BACKGROUND OF THE INVENTION

Scanned beam microscopy systems, including charged particle beam systems such as electron beam and focused ion beam (FIB) systems, are widely used in characterization or treatment of materials on a microscopic scale. For example, focused ion beam systems are used in manufacturing operations because of their ability to image, etch, mill, deposit and analyze with great precision. Ion columns in FIB systems using gallium liquid metal ion sources (LMIS), for example, can provide five to seven nanometer lateral imaging resolution.

The beam of a scanning beam system typically scans the surface of a target specimen in a raster pattern. This raster pattern may be used to produce an image of the surface of the target. When the scanned beam strikes the target, particles or photons are emitted from the immediate vicinity of beam impact. A portion of these emissions are measured or collected using a suitable detector or collector that produces an output signal indicative of the intensity of the emission. This output signal is then processed to produce an observable image displayed on a conventional video monitor.

A typical application of scanning beam systems is for analysis and treatment of integrated circuits (IC). In this application, a focused ion beam is used to produce an image of the circuit. This image is then used in conjunction with circuit layout information to navigate the ion beam over the surface of the circuit to locate a specific element or feature of interest. When the beam is scanned to the local area of interest, the beam current can be increased to cut into the circuit die and expose circuit features buried in layers. The FIB system can then alter the exposed circuit by cutting conductive traces to break electrical connections or by depositing conductive material to provide new electrical connections. This etching or deposition is caused by a physical or chemical reaction of the beam ions with the specimen and occurs at a rate that is largely dependent upon the constituent ions of the beam, the presence and type of etch enhancing or deposition precursor gases, and the beam current.

Also important in achieving accurate characterization and treatment of a specimen is the beam dwell time. The beam dwell time is the duration of time the beam dwells in a specific location on the specimen. In a scanned beam system, the beam is typically controlled by digital electronics to scan across the specimen in a stepwise fashion from point to point, dwelling for a pre-determined time at each point. The distance between the sample points at which the beam dwells is referred to as the pixel spacing or pitch. When imaging the surface, if the dwell time is too short for a given beam current, insufficient collection of emissions occurs to accurately characterize the surface at the dwell point. When this occurs, the displayed image will appear "noisy" because of a low signal-to-noise ratio.

A focused ion beam, even at relatively low energy, will always cause some destructive etching of the specimen surface. Even an electron beam can alter the specimen, for example, through electron-beam induced chemical reactions that cause hydrocarbons residual in the vacuum chamber to stain the sample surface. Because a charged particle beam will invariably cause changes in the specimen surface, a long dwell time will alter the surface, thereby decreasing the accuracy of the surface characterization. Thus, careful control of the beam intensity and dwell time at each point in the scan is required.

Further, the beam must be accurately focused and compensated for aberrations to provide a useful image of the specimen surface for visual or automated analysis. In a conventional method for focusing the beam, a calibration specimen is prepared consisting of an etched region or region of deposited material to form a target of well-defined shape upon which to focus the beam. When the beam is properly focused, the target shape will appear on a visual display in high contrast to the surrounding specimen surface. Once accurate focus is achieved, the calibration specimen is removed and the specimen to be analyzed or treated is placed in the plane of focus.

Unfortunately, to obtain a finely detailed image of the calibration specimen suitable for achieving sharp focus and precise calibration, many closely spaced samples of the target must be taken. When the pixel spacing is less than the beam spot size—typically defined as the beam diameter for which the beam drops to one-tenth of its maximum value—the problem of specimen degradation is exacerbated by the resultant high ion dose at each sample point. This degradation occurs at a rate that is sufficiently high to interfere with beam calibration. Conversely, if the beam current or dwell time is reduced to avoid this, then the signal-to-noise ratio decreases, resulting in a poor image of the calibration specimen that is unsuitable for achieving sharp focus and precise beam calibration. Further, using conventional scanning methods, fine calibration to remove small errors is difficult to achieve.

Thus, there is a need for methods and systems to achieve accurate scanned beam system calibration that overcome these and other limitations of the prior art.

SUMMARY OF THE INVENTION

The present invention provides for accurate calibration of a scanned beam system that overcomes limitations of the prior art. According to the methods of the present invention, a calibration specimen comprising an array of targets is sampled with a sample spacing that is greater than the spacing between the targets and an image is reconstructed from the samples.

The present invention enables achievement of very sharp beam focus and highly precise calibration without substantial degradation of the calibration specimen caused by closely spaced sampling. Slower scan speeds may be employed which provide an image of high contrast because of improved signal-to-noise ratio. Because the reconstructed image is composed of points spread at relatively large distances across the calibration specimen, beam aberrations and alignment errors are magnified and can be more readily corrected than when prior art calibration techniques are employed.

Application of the aliased image scanning technique of the present invention will magnify the effect of rotational misalignment of the calibration specimen with respect to the scan axes of the beam, enabling easier detection and correction of rotational misalignment. Also, conditions giving rise to a non-orthogonal relationship between the x-y axes of the image produced by the system are also magnified and can therefore be more easily detected and corrected. Further, beam stigmation effects are magnified for easier detection and correction. The invention is particularly well suited for use with automatic focusing and other automatic beam adjustments because it is very clear when the proper focus and other compensations are achieved.

The foregoing has rather broadly outlined features and technical advantages of the present invention in order that the detailed description of the invention that follows may be better understood. Additional features and advantages of the invention will be described hereinafter. It should be appreciated by those skilled in the art that the conception and specific embodiment disclosed herein may be readily utilized as a basis for modifying or designing other structures for carrying out many useful purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE PREFERRED EMBODIMENTS

Figure 1:
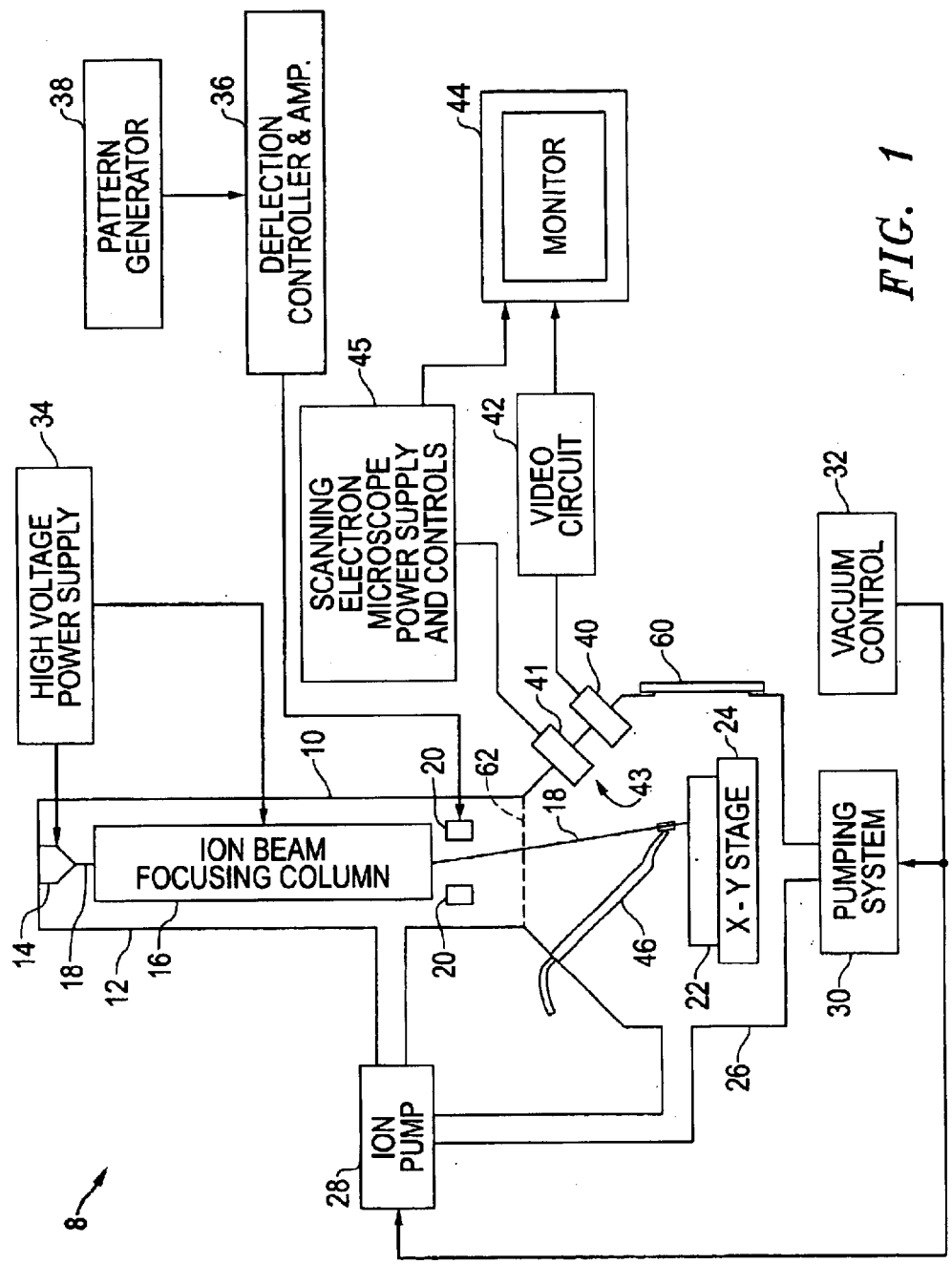
FIG. 1 shows schematically a typical focused ion beam system used in a preferred embodiment of the invention.

In a preferred embodiment of the invention, a calibration specimen is provided that comprises an array of calibration targets. The calibration specimen is sampled with a sample spacing that is greater than the spacing of the targets in the array. A composite image is formed from these samples and displayed.

According to the present invention the calibration targets are preferably arranged into a two-dimensional array of targets with equally spaced rows and equally spaced columns. The beam of the scanning beam system is scanned in a step-wise fashion to form a rectangular grid of sample points or pixels, one in each target. The horizontal distance between sample points in a row of targets is slightly greater than the horizontal spacing of the targets in the row. Thus, the sample taken from each target in a row is in a different horizontal position within the target than the horizontal position of the sample points within the other targets. Similarly, the vertical distance between each row of samples in a column of targets is slightly greater than the vertical spacing of the targets in the column. Thus the sample taken from each target in a column is in a different vertical position within the target than the vertical position of the sample points within the other targets. The samples from each target are assembled to form an image of the target shape that is used to achieve calibration of the beam.

To obtain a reconstructed image of the target samples, the beam may be scanned across each row successively or, alternatively, down each column successively. Other sampling patterns and target patterns may be used, so long as the relative positions of each sample point and target location are defined so that an image of the shape may be formed from the samples. Formation of the reconstructed image shape may be performed continually by repeatedly sampling the array of targets and displaying the sample points obtained by each complete scan of the specimen. This allows the operator to calibrate the system while visually monitoring the effect of his or her adjustments. Since the samples taken during a complete scan of the calibration specimen according to the methods of the present invention are widely spaced—much greater than the beam spot size—the cumulative particle dose at any point on the sample is greatly reduced, with a consequent reduction in specimen surface damage. Moreover, with suitable processing, the positions of each sample within each target can be different for each different complete scan of the calibration specimen so that the same point within a target is not sampled more than once in any set of complete scans of the array.

The present invention will be discussed in the context of use in a focused ion beam system for demonstrative purposes. However, it will be understood that the methods of the present invention may also be employed in other scanned systems, such as electron beam systems including scanning electron microscopes and scanning transmission electron microscopes, and scanning probe microscopes, such as scanning tunneling microscopes and atomic force microscopes.

In FIG. 1, a focused ion beam system 8 includes an evacuated envelope 10 having an upper neck portion 12 within which are located a liquid metal ion source 14 and a focusing column 16 including extractor electrodes and an electrostatic optical system. Ion beam 18 passes from source 14 through column 16 and between electrostatic deflection mechanism schematically indicated at 20 toward specimen 22, which comprises, for example, a semiconductor device positioned on movable X-Y stage 24 within lower chamber 26. An ion pump 28 is employed for evacuating neck portion 12. The chamber 26 is evacuated with turbo-molecular and mechanical pumping system 30 under the control of vacuum controller 32. The vacuum system provides within chamber 26 a vacuum of between approximately $1 \times 10^{-7}$ Torr and $5 \times 10^{-4}$ Torr. If an etch-assisting or an etch-retarding gas is used, the chamber background pressure is typically about $1 \times 10^{-5}$ Torr.

High voltage power supply 34 is connected to liquid metal ion source 14 as well as to appropriate electrodes in focusing column 16 for forming an approximately 1 keV to 60 keV ion beam 18 and directing the same downwardly. Deflection controller and amplifier 36, operated in accordance with a prescribed pattern provided by pattern generator 38, is coupled to deflection plates 20 whereby beam 18 may be controlled to trace out a corresponding pattern on the upper surface of specimen 22. In some systems the deflection plates are placed before the final lens, as is well known in the art.

The source 14 typically provides a metal ion beam of gallium, although other ion sources, such as a multi-cusp or other plasma ion source, can be used. The source typically is capable of being focused into a sub-one-tenth micron wide beam at specimen 22 for either modifying the surface 22 by ion milling, enhanced etch, material deposition, or for the purpose of imaging the surface 22. A charged particle multiplier 40 used for detecting secondary ion or electron emission for imaging is connected to video circuit and amplifier 42, the latter supplying drive for video monitor 44 also receiving deflection signals from controller 36. The location of charged particle multiplier 40 within chamber 26 can vary in different embodiments. For example, a preferred charged particle multiplier 40 can be coaxial with the ion beam and include a hole for allowing the ion beam to pass. A scanning electron microscope 41, along with its power supply and controls 45, are optionally provided with the FIB system 8.

A fluid delivery system 46 optionally extends into lower chamber 26 for introducing and directing a gaseous vapor toward sample 22. U.S. Pat. No. 5,851,413 to Casella et al. for "Gas Delivery Systems For Particle Beam Processing," assigned to the assignee of the present invention, describes a suitable fluid delivery system 46.

A door 60 is opened for inserting specimen 22 on stage 24 which may be heated or cooled, and also for servicing the reservoir 50. The door is interlocked so that it cannot be opened if the system is under vacuum. The high voltage power supply provides an appropriate acceleration voltage to electrodes in ion beam column 16 for energizing and focusing ion beam 18. When it strikes specimen 22, material is sputtered, that is physically ejected, from the sample. Focused ion beam systems are commercially available, for example, from FEI Company, Hillsboro, Oreg., the assignee of the present application.

Signals applied to deflection controller and amplifier 36 cause the focused ion beam to move within a target area to be imaged or milled according to a pattern controlled by pattern generator 38. Ideally, the beam converges in the plane of the specimen in a circle. However, if the system is not calibrated, the beam may converge before or after the sample plane causing the image to be unfocussed. Also, the beam may exhibit stigmatic effects. For example, the beam may be more elliptical than circular. Moreover, there may be rotational misalignment between the axes of the specimen and the scan axes of the beam. Or there may exist a non-orthogonal relationship between the beam axes. Further, the scan gain may be different in each of the orthogonal scan directions so that in one direction the image appears "stretched". The scanned beam system must therefore be calibrated to eliminate or at least minimize these errors. Typically, a scanned beam system will provide control elements to achieve calibration. For example, an electrostatic lens system is provided to cause the beam to converge at the correct focal point and a stigmator is provided to adjust for stigmation effects.

To calibrate the system, a calibration specimen is provided that contains a well defined target or pattern formed of etched or deposited regions of the specimen to create an image of high visual contrast to the surrounding specimen surface. For example, a typical calibration specimen may comprise a sequence of parallel lines etched into the specimen. When the calibration specimen is scanned, charged particle multiplier 40 collects the emissions from each sample point, and an image is displayed on video monitor 44 by way of video circuit 42. An operator viewing the image may adjust the voltages applied to the various control elements to focus the beam and adjust the beam for various aberrations.

In the conventional method of scanning, a detailed image of the specimen is obtained by densely sampling the specimen with many closely spaced sample points. If the sampling density is so great that the pixel spacing is less than the beam spot size there exists overlap of the beam energy at adjacent pixels. This increases the rate at which the surface of the specimen is degraded by the interaction of the beam and the surface. A high rate of degradation decreases the time available for the operator of the scanned beam system to achieve calibration. Further, as will be explained in more detail subsequently, small calibration errors are difficult to detect from analysis of the image formed by the conventional scanning method, making fine calibration very difficult to achieve.

In contrast to the conventional method of scanning the calibration specimen using a high sampling density, the present invention provides for sampling a specimen containing an array of targets etched or deposited thereon with spacing between samples that is greater than the spacing between targets in the array. The targets are preferably of substantially identical shape and size and are equally spaced in each of the two orthogonal axes in the plane of the specimen. Thus, along the x-axis, the spacing between each target is $P_x$, and along the y-axis the target spacing is $P_y$. The spacing between sample points in the x-direction is greater than the target spacing in the x-direction. Thus, the x-directed spacing between samples is $nP_x+dx$ where n is an integer and $dx \ll P_x$. Similarly, the spacing between sample points in the y-direction is greater than the target spacing in the y-direction. Thus, the y-directed spacing between samples is $mP_y+dy$ where m is an integer and $dy \ll P_y$.

By sampling the array of targets in this way, each target is sampled at a different point there within. These samples are then assembled to construct an image of the specimen. Because the sample points are widely spaced apart a finely detailed image can be formed without the rapid degradation of the specimen associated with dense sampling of the specimen. Thus, the calibration specimen will remain stable for a much greater period of time. Moreover, longer dwell times and slower scans can be employed without degrading the specimen, resulting in a high signal-to-noise ratio. This in turn results in an image of high contrast with respect to the background. Further, because the sample points forming the image are distributed over a much larger field of view, an image that is a more sensitive function of beam focus, stigmation, and alignment is obtained, thus enabling the operator to achieve a very fine calibration of the system.

The method of the present invention can be better understood by modeling the one-dimensional spatial response of a specimen of an array of targets to a scanned beam microscope as a periodic function, $f$, of period P. In the case of a scanning electron microscope (SEM) or a focused ion beam system (FIB), for example, $f$ might describe a relative secondary-electron emission intensity signal at each sample point of the specimen in response to the beam. In the case of a scanned laser microscope, for example, $f$ might be proportional to the relative reflectivity of the specimen at each sample point. Let $f$ be written as follows:

$$f(x,P)=\sin^2(\pi x/P)$$

The corresponding two-dimensional spatial response function of the two-dimensional array of targets is given by:

$$f(x,y,P_x,P_y)=\sin^2(\pi x/P_x)\sin^2(\pi y/P_y)$$

Figure 2:
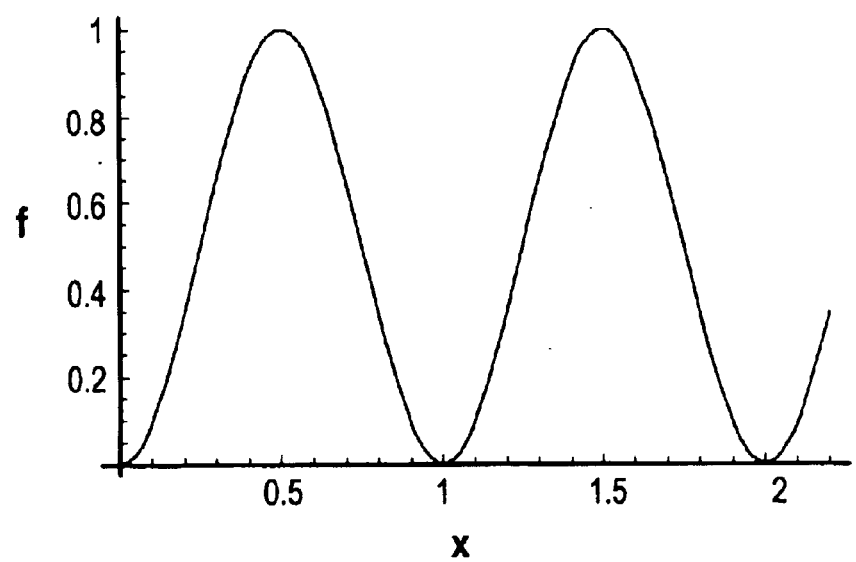
FIG. 2 shows a one-dimensional periodic spatial response function: a sine-squared function with a period, P, of 1 micro-meter ($\mu$m).
Figure 3:
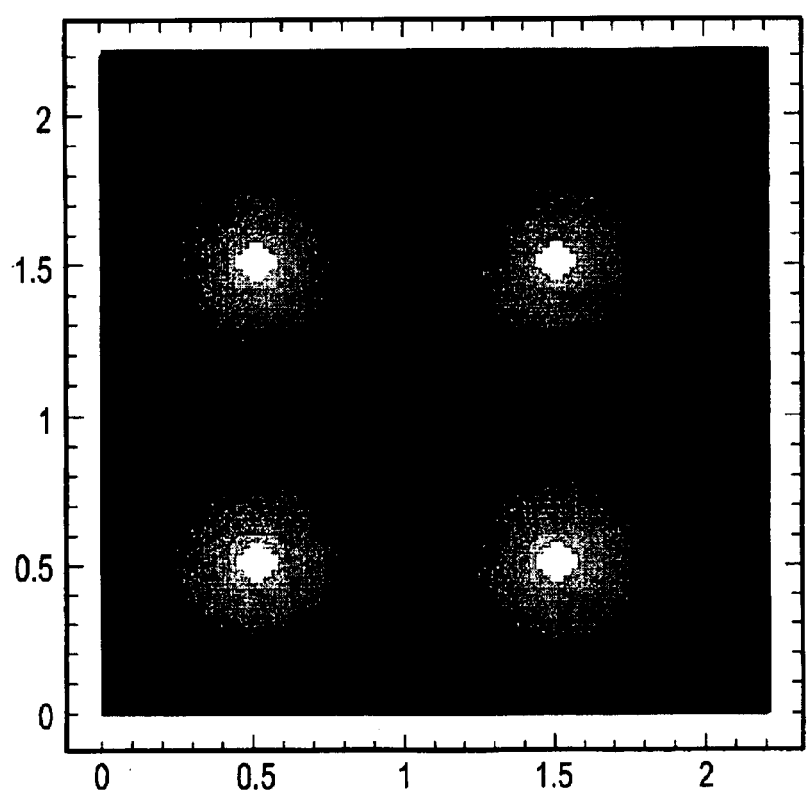
FIG. 3 shows a two-dimensional periodic spatial response function: a sine-squared function of x and y with a period, P, of 1 $\mu$m in each direction.

For clarity of exposition, let $P_x=P_y=P=1$ micro-meter (1 μm), understanding that the invention is not limited to equal periods in the x and y directions. Plots of $f(x, P)$ and $f(x, y, P)$ are shown in FIGS. 2 and 3.

Conventionally, the scanned beam will sample the specimen with a sample pitch, ds, that is small compared to the target periodicity, P, to provide a fine image of the targets in the specimen. Suppose, for example, that ds=P/Q, where Q is the number of samples per period. The beam samples the specimen with a finite number of samples, N, where in a typical system N is 256, 512, or 1024. The field of view, F, is given by F=(N−1)ds. For example, with P=1 μm, N=256 and Q=40, the field of view of the specimen is F=6.375 μm.

Figure 4:
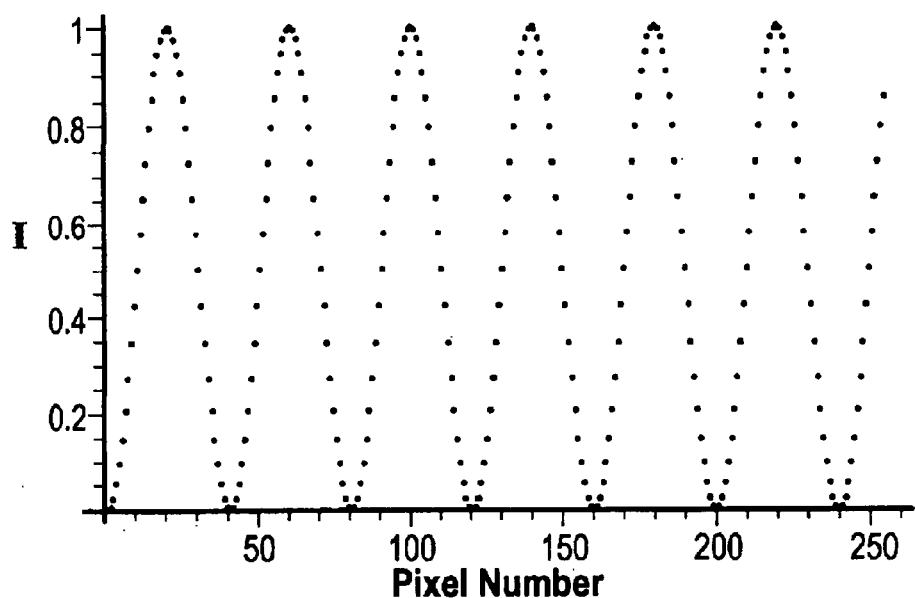
FIG. 4 shows conventional sampling of a one-dimensional periodic spatial response function with a sampling pitch of ds=P/40.
Figure 5:
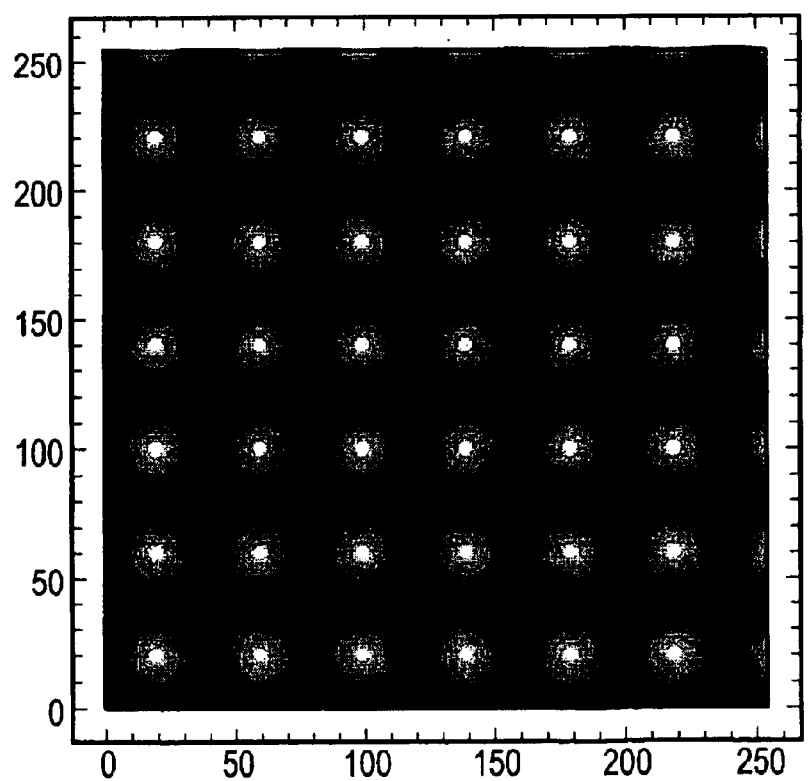
FIG. 5 shows conventional sampling of a two-dimensional periodic spatial response function with a sampling pitch of ds=P/40 in each direction.

The N samples taken of the specimen are mapped to an identical number of pixels in the display of video monitor 44. A gray scale is used to show the intensity of the signal received at each sample point. When plotted as a function of pixel number along the scanned axis of the specimen, the graph of intensity appears as in FIG. 4. The corresponding 2-dimensional image is shown in FIG. 5 with equal pitch, ds, and period, P, in both the x and y directions. The pitch of the display pixels, dp, will be different from the sampling pitch, ds. For example, if dp=300 μm, the length, L, of the image of the specimen displayed on the screen is L=(N−1)dp=76,500 μm for N=256. The linear magnification, M, of the system is given by M=L/F=dp/ds=12000. By reducing the sampling pitch by one-half, for example, the magnification, M, can be doubled, reducing the field of view, F, by one-half.

Figure 6:
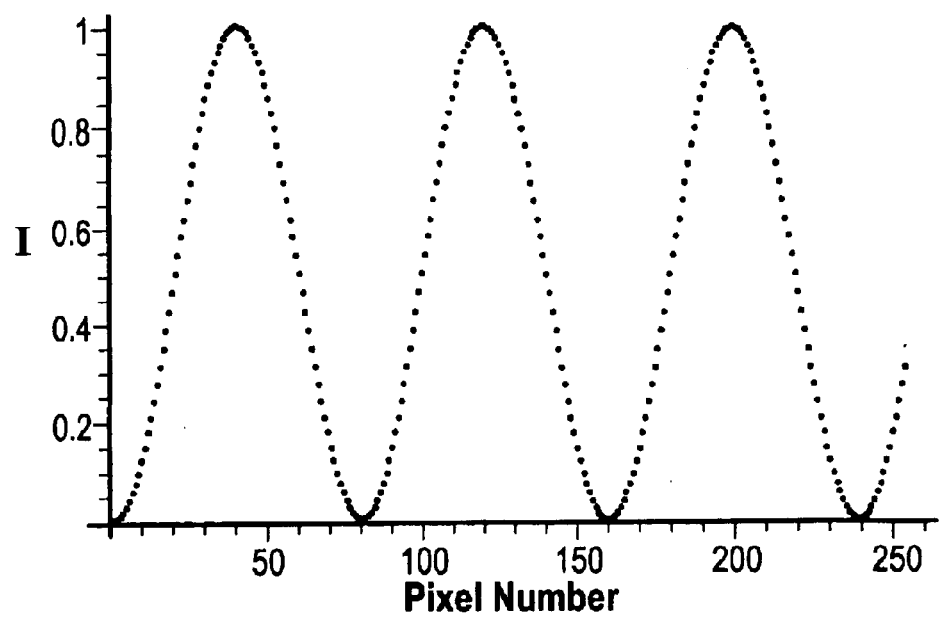
FIG. 6 shows conventional sampling of a one-dimensional periodic spatial response function with a sampling pitch of ds=P/80.
Figure 7:
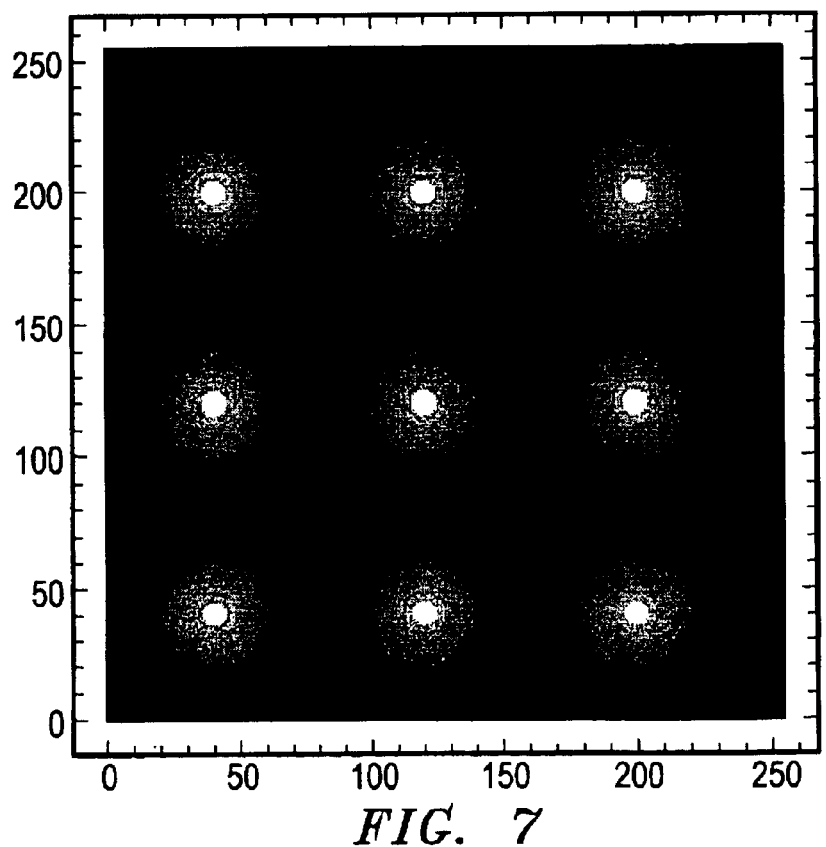
FIG. 7 shows conventional sampling of a two-dimensional periodic spatial response function with a sampling pitch of ds=P/80 in each direction.

Consider the images shown in FIGS. 6 and 7 which are obtained using a conventional sampling pitch of ds=P/80 with P=1 μm. As can be seen, the dense sampling results in a finely detailed image of the targets of the specimen. However, dense sampling also results in target degradation due to the closeness of the samples, as previously discussed. The present invention provides a sampling method that avoids these limitations of the prior art. In a preferred embodiment the sample pitch is greater than the target periodicity, P, but less than 2P, so that the beam scans the specimen with one and only one sample per target. This is accomplished by choosing as the sampling pitch, ds':

$$ds'=nP+ds$$

where n is an integer normally chosen equal to 1, and assumed to be equal to 1 herein unless otherwise noted.

Figure 8:
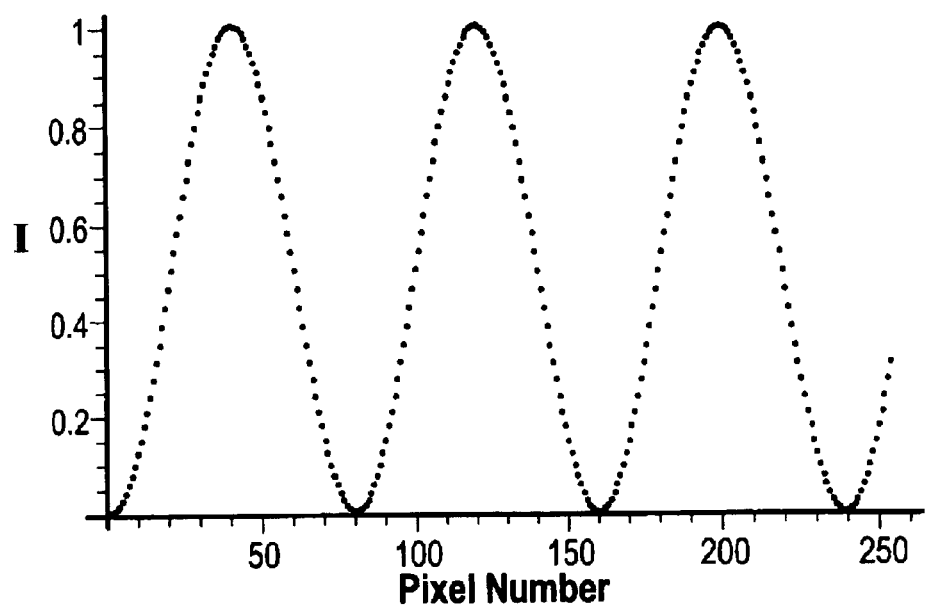
FIG. 8 shows aliased image sampling of a one-dimensional periodic spatial response function with a sampling pitch of ds'=P+P/80.
Figure 9:
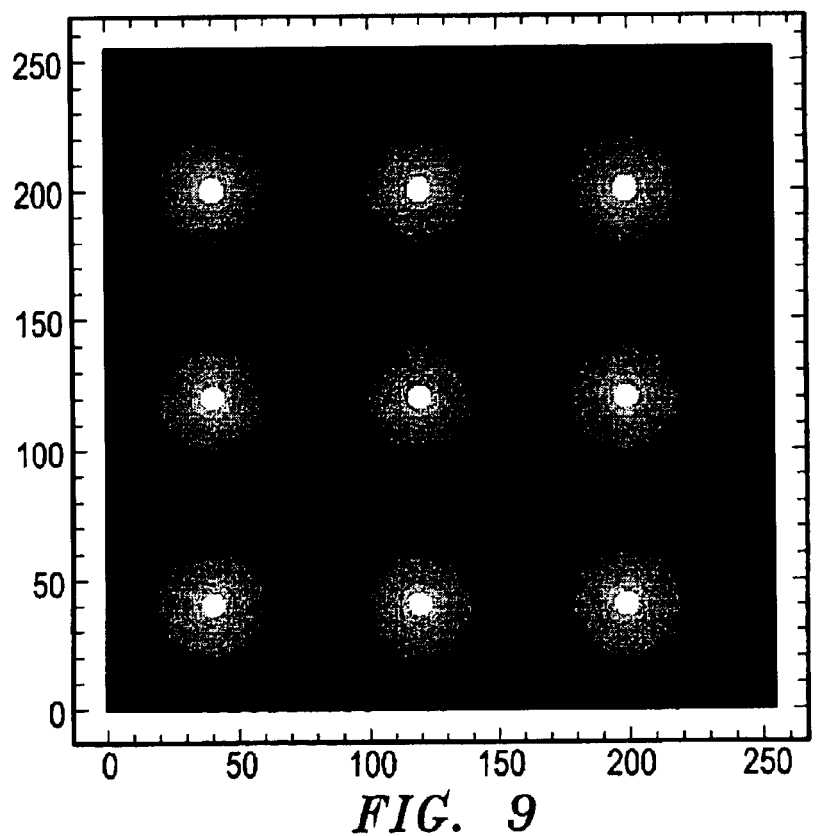
FIG. 9 shows aliased image sampling of a two-dimensional periodic spatial response function with a sampling pitch of ds'=P+P/80 in each direction.

For example, let P=1 μm and ds=P/80. Then ds'=1.0125 μm. Once again choosing N=256, the field of view, F', is equal to (N−1)ds'=258.188 μm. Thus, the sampling pitch, ds', yields a field of view, F', that is substantially larger than the field of view, F, that is obtained with a sampling pitch of ds. The linear sampling point density has decreased by a factor of ds'/ds=81. In two dimensions, the reduction in sampling point area density is $(ds'/ds)^2=6561$. The resultant image is shown in FIGS. 8 and 9. Note that identical images are obtained whether the sampling point density, ds, or the sampling point density, ds'=P+ds, is used. This is seen by comparison of FIGS. 6 and 7 and FIGS. 8 and 9.

The length of the displayed image, L', is the same as the length of the displayed image from the conventional method of sampling with pitch, ds. That is, L'=L. Note however, that the magnification, M'=L'/F', of the aliased, scanned image is much lower than the magnification obtained from sampling the image in the conventional manner, since the field of view obtained from the larger sampling pitch is much greater. However, the apparent magnification, $M_A$, is the same as the magnification obtained from the conventional method. This is explained as follows. In aliased image scanning, each successive sample along the scanning axis lands one incremental distance, ds, further relative to the beginning of each period. Thus, one complete period is sampled after a number of samples, Q=P/ds. The length, $L_A$, of one reconstructed period on the display is Qdp, where dp is the display pitch, assumed in the example given above to be 300 μm. The apparent magnification is, therefore, $M_A=L_A/P=dp/ds=24,000$. This is the same magnification as obtained from conventional sampling, using the sampling pitch ds. The ratio of the apparent magnification to the actual magnification, $R=M_A/M'$, is equal to ds'/ds.

Using the above-defined relationships between conventional scanning and aliased image scanning, various advantages and uses of the aliased image scanning technique of the present invention will now be described.

Figure 10:
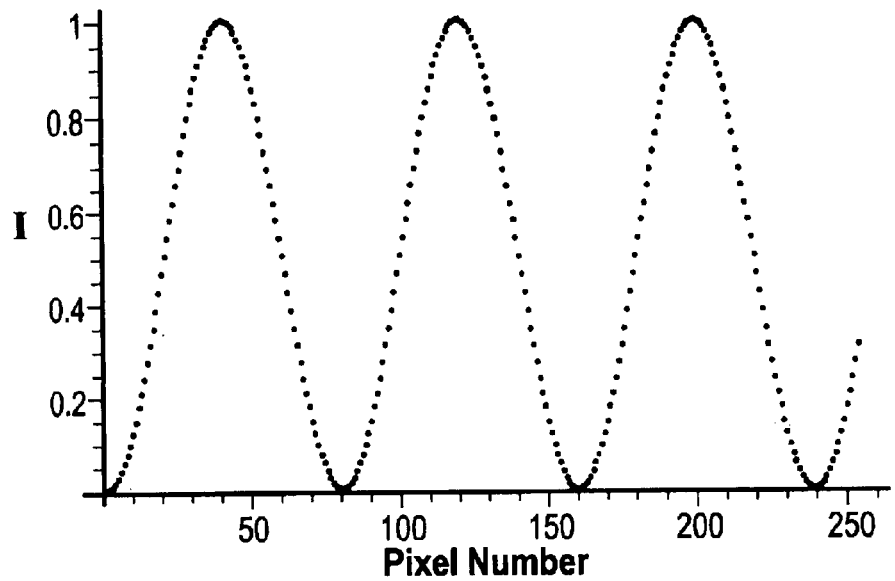
FIG. 10 shows conventional sampling of a one-dimensional periodic spatial response function with a sample pitch of ds=1 $\mu$m/80: the period of the spatial response function is 1 $\mu$m.
Figure 11:
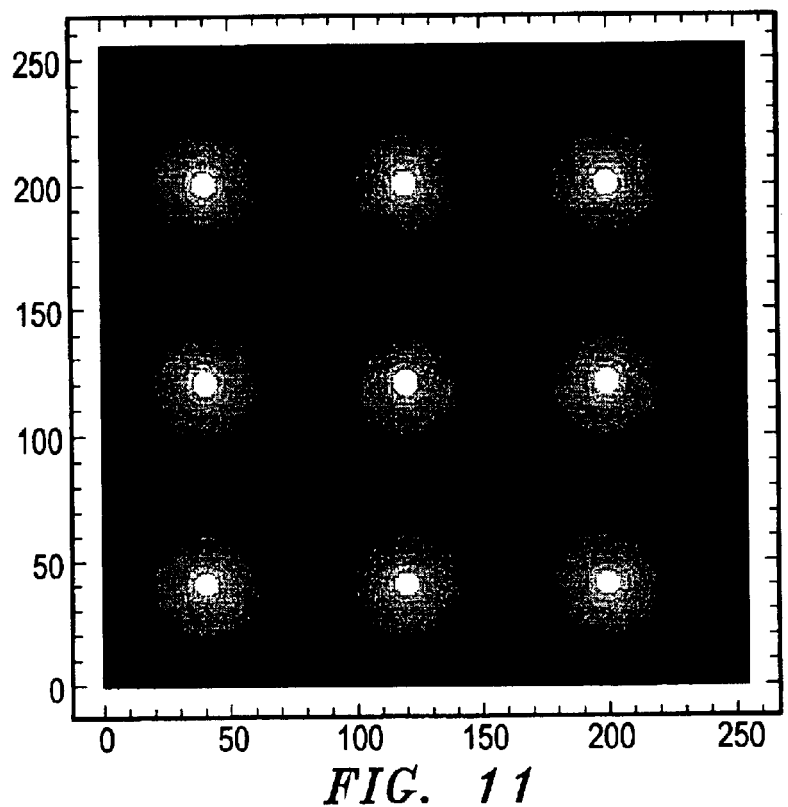
FIG. 11 shows conventional sampling of a two-dimensional periodic spatial response function with a sample pitch of ds=1 $\mu$m/80 in each direction: the period of the spatial response function is 1 $\mu$m in each direction.
Figure 12:
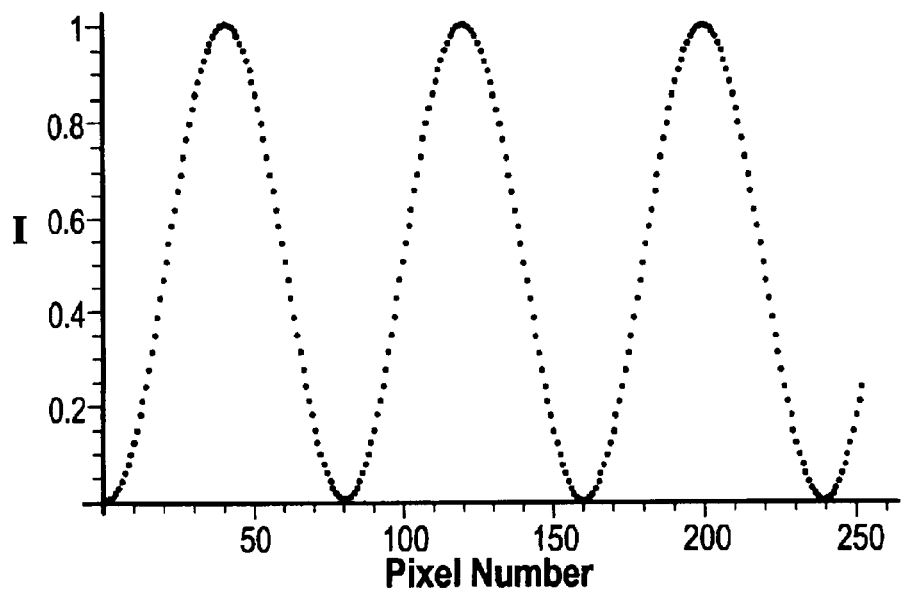
FIG. 12 shows conventional sampling of a one-dimensional periodic spatial response function with a sample pitch of ds=1 $\mu$m/80: the period of the spatial response function is 1.01 $\mu$m.
Figure 13:
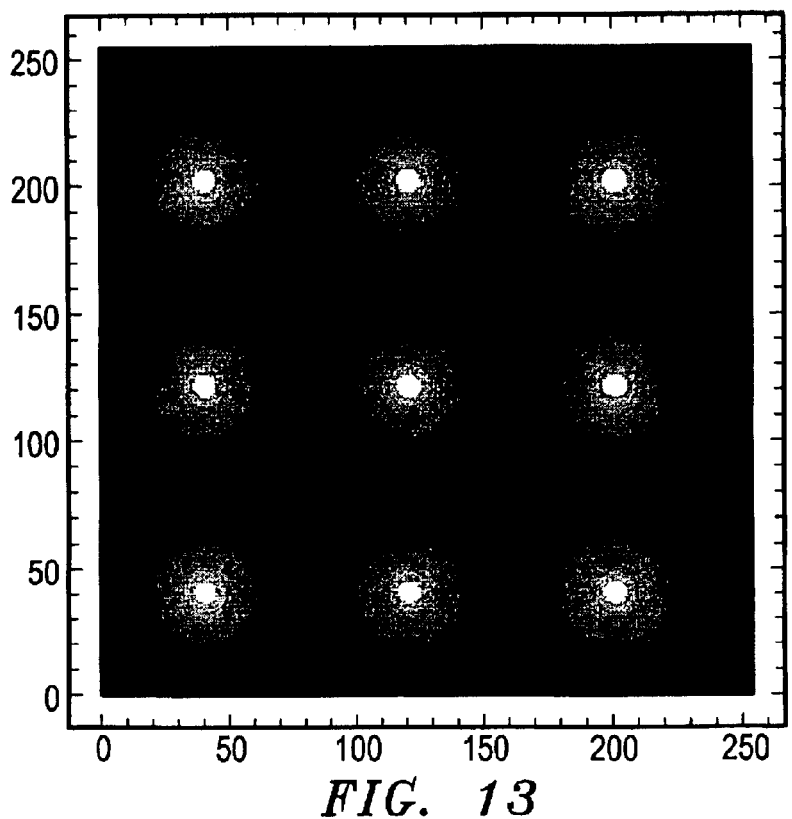
FIG. 13 shows conventional sampling of a two-dimensional periodic spatial response function with a sample pitch of ds=1 $\mu$m/80 in each direction: the period of the spatial response function is 1.01 $\mu$m in each direction.

Suppose that the expected target periodicity, $P_E$, varies from the actual periodicity, $P_A$, by a small amount, $\Delta P$: that is, $P_A = P_E + \Delta P$. One might expect this offset in periodicity to result from a scan field calibration error, or a misplacement of the sample surface with respect to an expected working height. To illustrate, suppose that $P_E = 1$ µm and $\Delta P = P_E 100$. Then $P_A = 1.01$ µm. Suppose the specimen were sampled according to the conventional method of using a sampling pitch much less than the expected period $P_E$, for example, $ds = P_E/80 = 0.0125$ µm. FIGS. 10 and 11 show the one- and two-dimensional results of scanning an image that has the expected period of 1 µm with a sampling pitch $ds = 0.0125$ µm. FIGS. 12 and 13 show the one- and two-dimensional results of scanning an image that has a period of 1.01 µm with the same sampling pitch, $ds = 0.0125$ µm. The difference between the images of the two specimens is barely perceptible, there being only a 1% difference in the length of the images.

Figure 14:
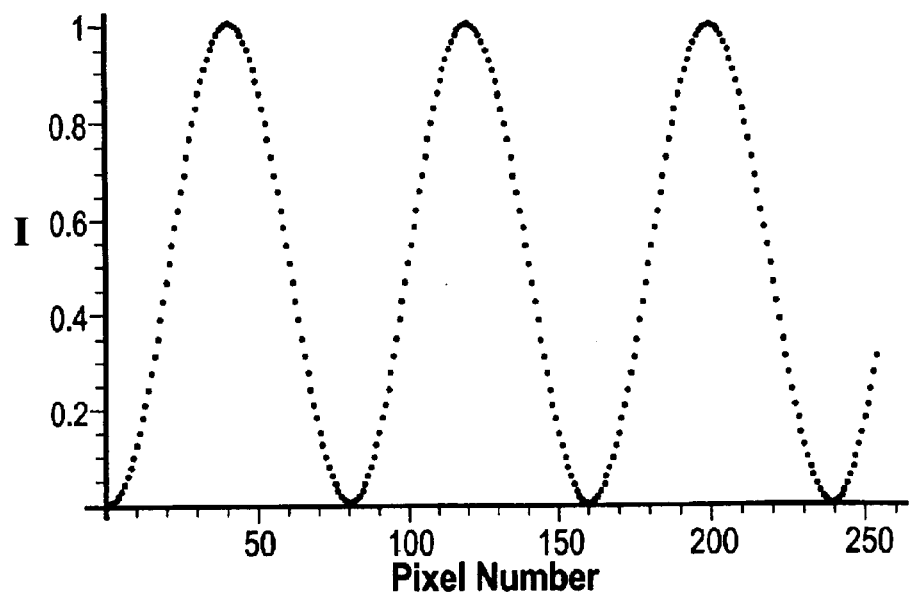
FIG. 14 shows aliased image sampling of a one-dimensional periodic spatial response function with a sample pitch of ds'=1 $\mu$m+1 $\mu$m/80: the period of the spatial response function is 1 $\mu$m.
Figure 15:
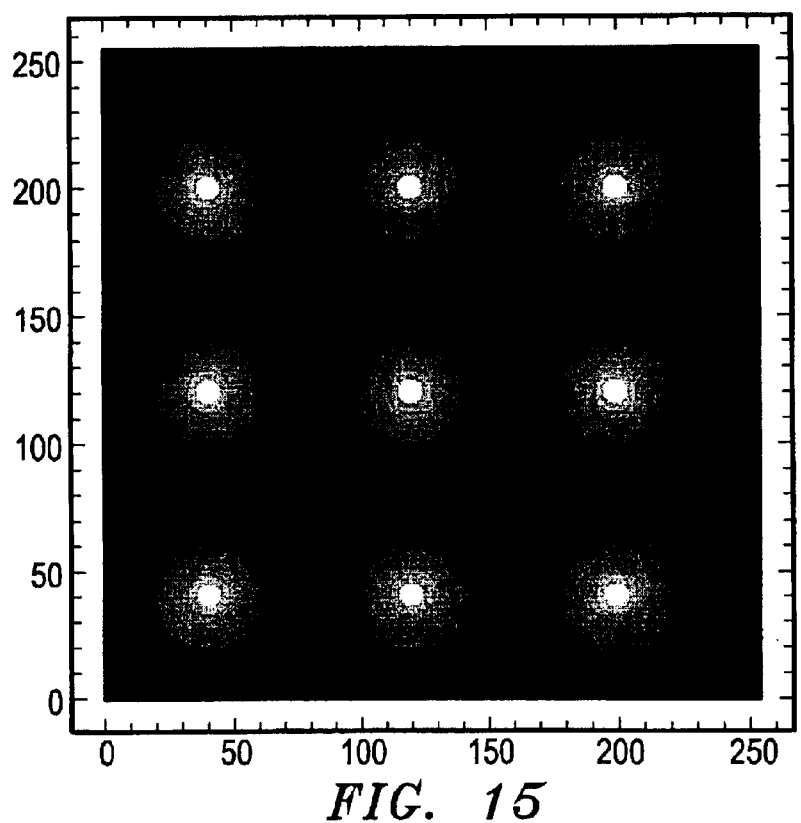
FIG. 15 shows aliased image sampling of a two-dimensional periodic spatial response function with a sample pitch of ds'=1 $\mu$m+1 $\mu$m/80 in each direction: the period of the spatial response function is 1 $\mu$m in each direction.
Figure 16:
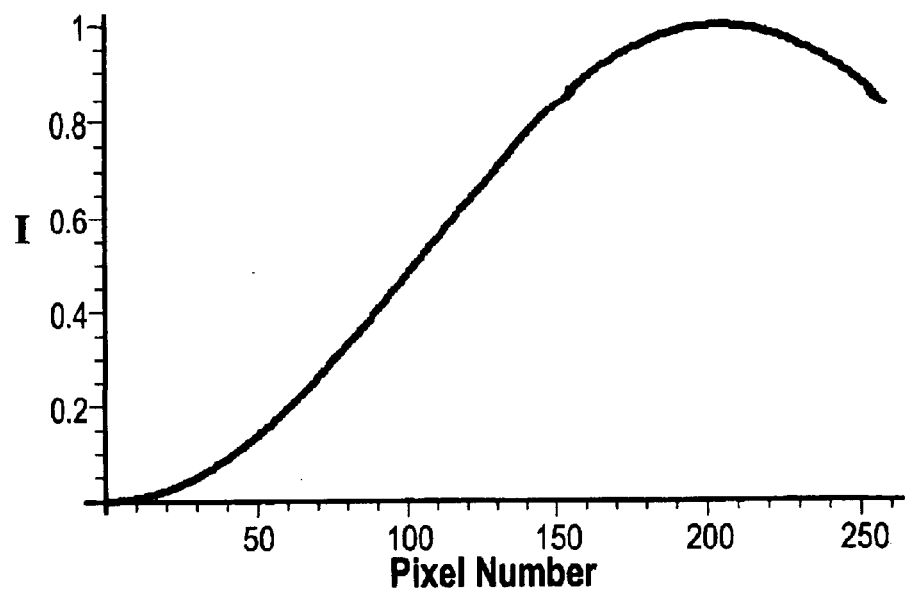
FIG. 16 shows aliased image sampling of a one-dimensional periodic spatial response function with a sample pitch of ds'=1 $\mu$m+1 $\mu$m/80: the period of the spatial response function is 1.01 $\mu$m.
Figure 17:
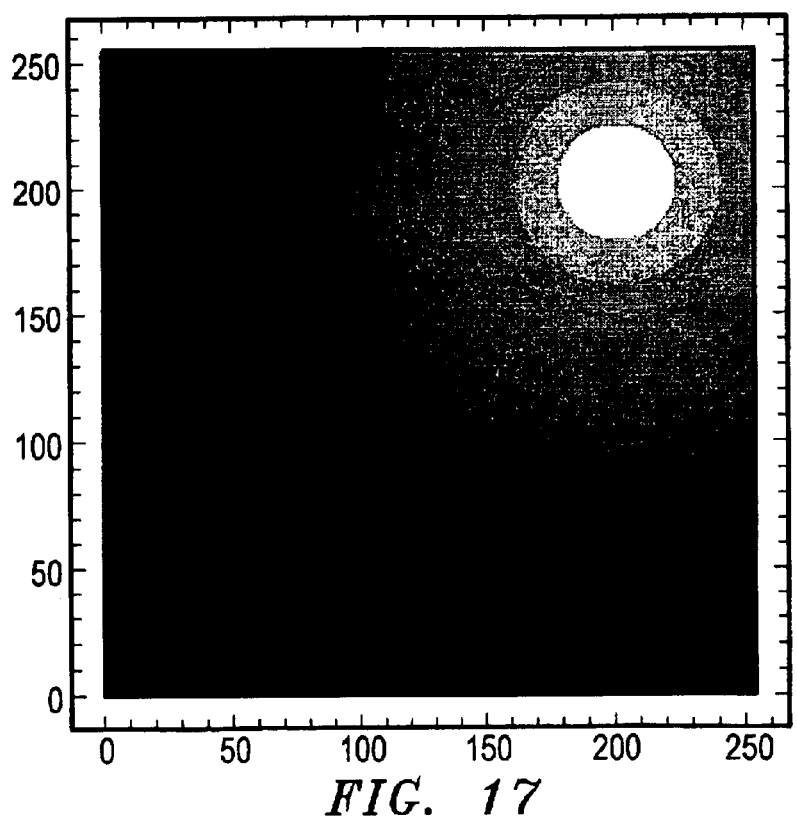
FIG. 17 shows aliased image sampling of a two-dimensional periodic spatial response function with a sample pitch of ds'=1 $\mu$m+1 $\mu$m/80 in each direction: the period of the spatial response function is 1.01 $\mu$m in each direction.

Now consider the result of scanning the two specimens, the one with a period of 1 µm and the other with a period of 1.01 µm, with the aliased image scanning technique of the present invention. Using a sampling pitch of $ds' = P_E + ds = 1.0125$ µm, the results of scanning the first specimen having the expected periodicity of 1 µm are shown in FIGS. 14 and 15, and the results of scanning the second specimen having the periodicity of 1.01 µm are shown in FIGS. 16 and 17. Clearly, the aliased imaging technique of the present invention results in a substantial difference between the images of the two specimens.

The increased sensitivity to the difference between the actual periodicity of the specimen and the expected periodicity used to pick ds' facilitates the use of the technique for highly accurate beam calibration. Since the change in the apparent magnification is so pronounced, it can be measured, and the value of $\Delta P$ can be derived there from.

The aliasing sample pitch, ds', can be expressed in terms of the unknown periodicity:

$$ds' = P_E + ds = (P_A - \Delta P) + ds = P_A + (ds - \Delta P)$$

In aliased sampling of the specimen with periodicity of $P_A$, each successive sample along the scanning axis lands one incremental distance, $ds - \Delta P$, further relative to the beginning of each period. Thus, one complete period is sampled after a number of samples, $$Q = \frac{P_A}{(ds - \Delta P)}.$$

The length, $L_A$, of one reconstructed period on the display is Qdp, where dp is the display pitch, assumed in the example given above to be 300 µm. The apparent magnification, $M_A = L_A/P_A$, expressed as a function of $\Delta P$, is therefore:

$$M_A(\Delta P) = \frac{dp}{ds - \Delta P}$$

Using this notation, we obtain the magnification relative to the magnification of the specimen with the expected periodicity, $P_E$:

$$\Gamma(\Delta P) = \frac{M_A(\Delta P)}{M_A(0)} = \frac{ds}{ds - \Delta P}$$

Figure 18:
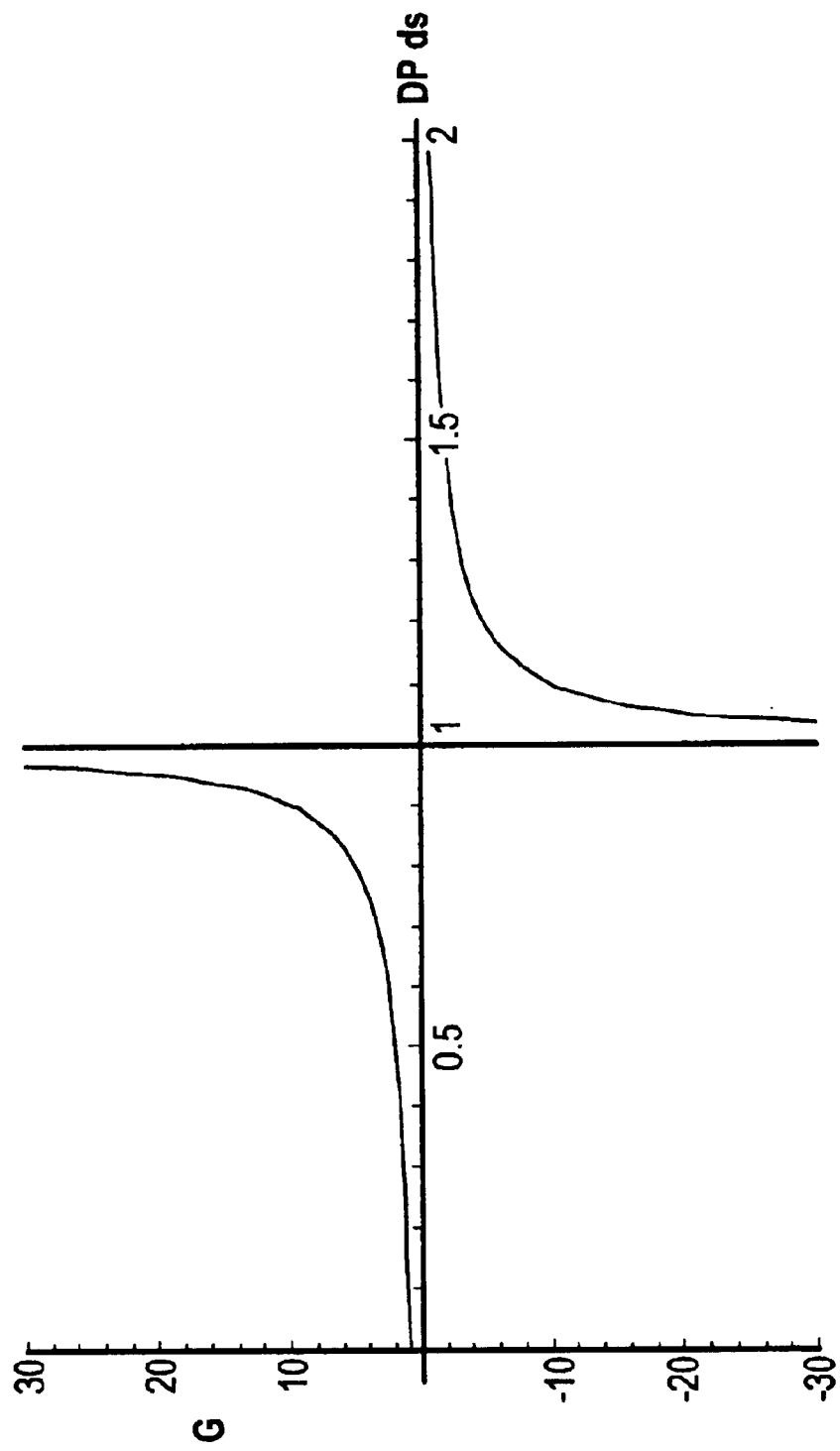
FIG. 18 shows a plot of relative variation in apparent magnification versus a normalized error in target periodicity.

Defining a dimensionless variable, $\delta = \Delta P/ds$, we have:

$$\Gamma(\Delta P) = \frac{1}{1 - \delta}$$

which is plotted in FIG. 18 as $\delta$ varies from 0 to 2. When $\Delta P = 0$, $\Gamma = 1$, and the apparent magnification is unchanged compared to the reference specimen of periodicity, $P_E$. As $\Delta P$ increases, the apparent magnification increases. In particular, as $\Delta P$ approaches +ds, $\delta$ approaches 1 and the magnification becomes very large.

Figure 19:
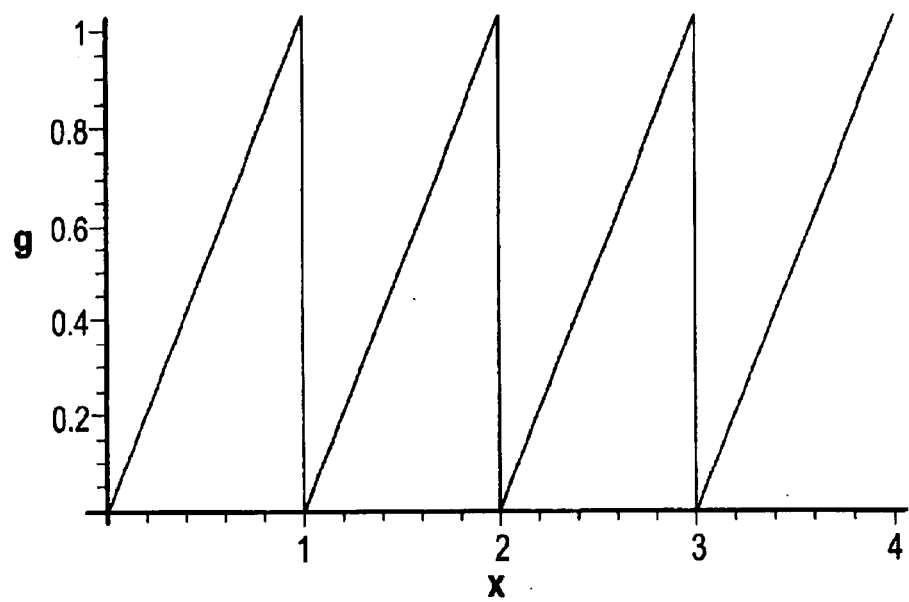
FIG. 19 shows a one-dimensional periodic spatial response function: a sawtooth function with a period, P, of 1 $\mu$m.
Figure 20:
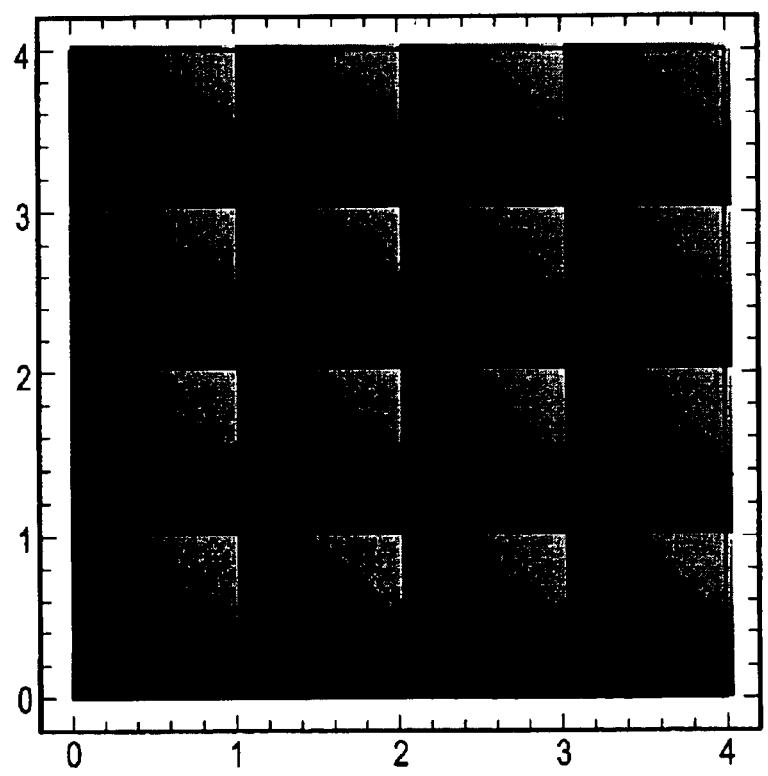
FIG. 20 shows a two-dimensional periodic spatial response function: a sawtooth function of x and y with a period, P, of 1 $\mu$m in each direction.

When $\delta$ is less than 1, corresponding to choosing $ds < \Delta P$, the function, $\Gamma$, reverses sign. This corresponds to a reversal of the image about the x-axis and the y-axis. To demonstrate this effect, a target that produces an asymmetric intensity pattern is used, such as shown in FIGS. 19 and 20. Assume that the saw-tooth pattern shown in FIG. 19 has a period of $P = 1$ µm. The one dimensional distribution can be described functionally as:

$$g(x) = \Lambda\left(\frac{x}{P}\right)$$

where the operator, $\Lambda$, denotes the periodic extension of the function (x/P) on the interval from x=0 to x=P. The corresponding two-dimensional function describing the distribution shown in FIG. 20 is:

$$g(x, y) = \Lambda\left(\frac{x}{P}\right)\Lambda\left(\frac{y}{P}\right)$$

where identical periodicity in both x and y directions is used for clarity of exposition.

Figure 21:
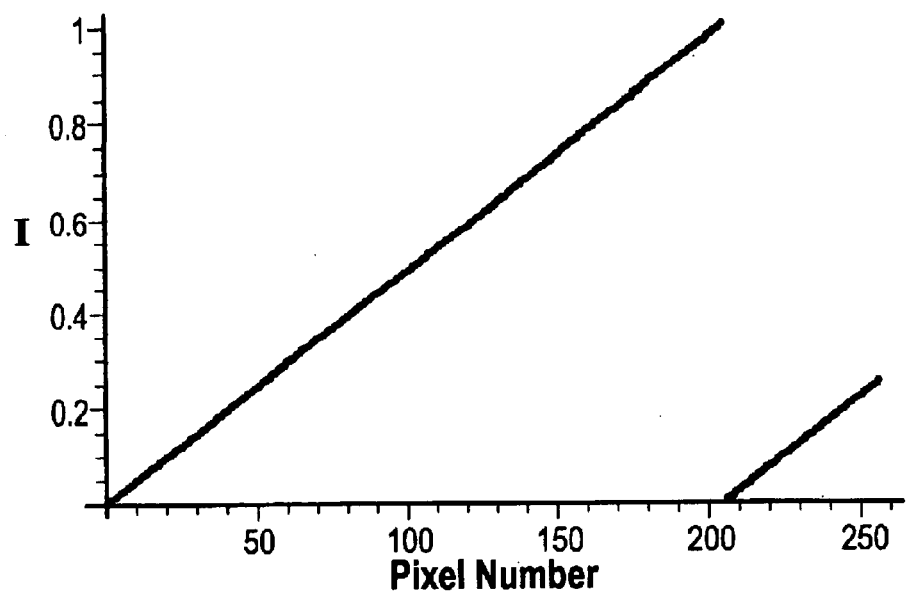
FIG. 21 shows aliased image sampling of a one-dimensional periodic spatial response function with a sampling pitch of ds'=P+P/40 and $\Delta$P/ds=0.8.
Figure 22:
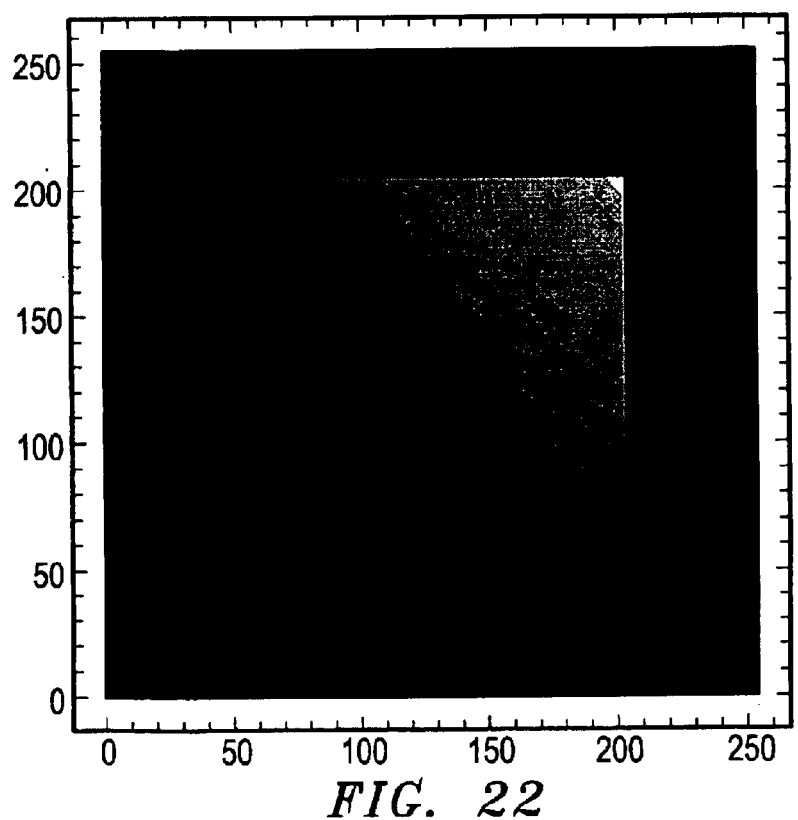
FIG. 22 shows aliased image sampling of a two-dimensional periodic spatial response function with a sampling pitch of ds'=P+P/40 and $\Delta$P/ds=0.8 in each direction.
Figure 23:
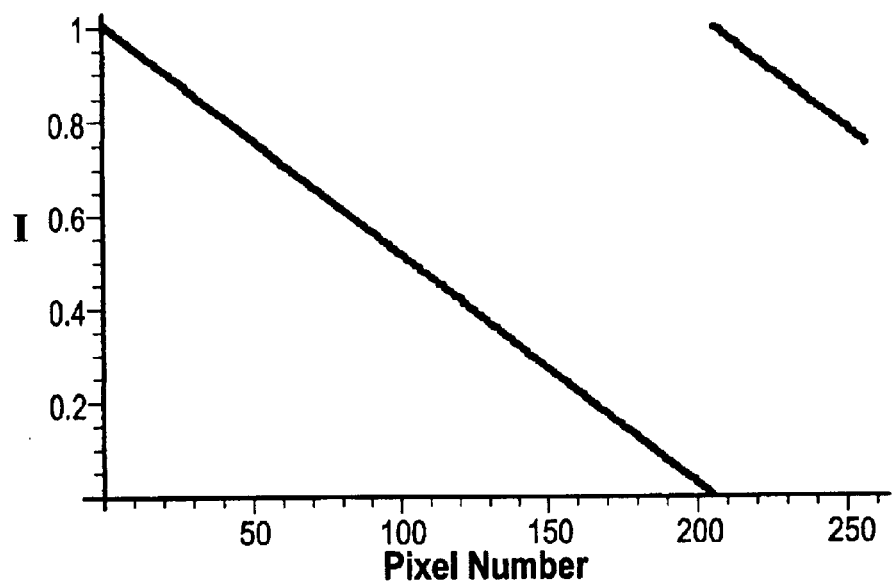
FIG. 23 shows aliased image sampling of a one-dimensional periodic spatial response function with a sampling pitch of ds'=P+P/40 and $\Delta$P/ds=1.2.
Figure 24:
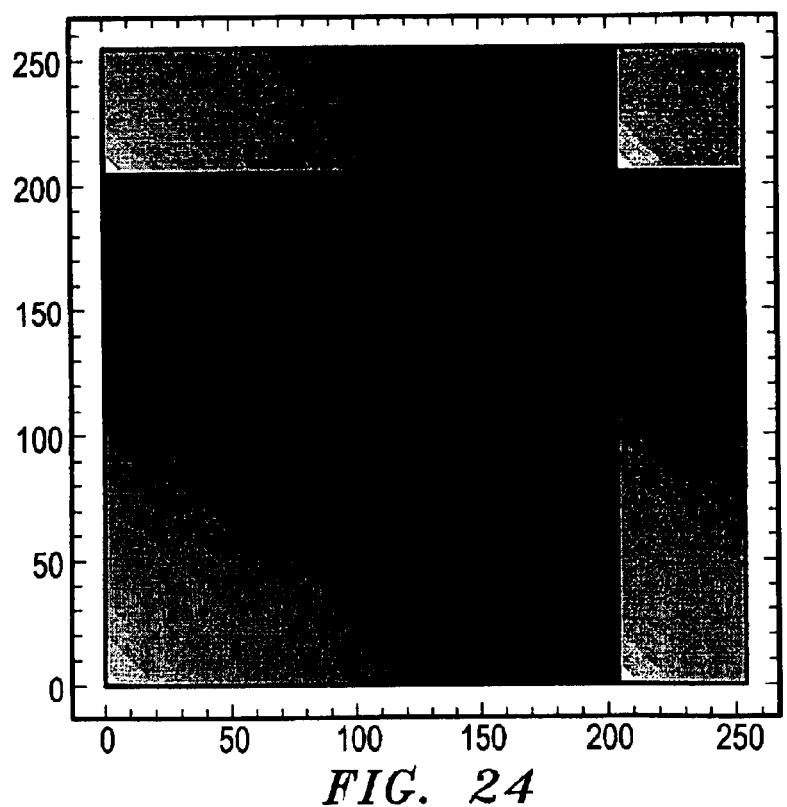
FIG. 24 shows aliased image sampling of a two-dimensional periodic spatial response function with a sampling pitch of ds'=P+P/40 and $\Delta$P/ds=1.2 in each direction.

Using a sampling pitch, ds, of $P/40 = 0.025$ µm results in an aliased image sample pitch, ds', of $P + ds = 1.025$ µm. To illustrate the image-reversing effect noted above, consider the two following cases:

a. $\Delta P = 0.8$ ds as shown in FIGS. 21 and 22; and b. $\Delta P = 1.2$ ds as shown in FIGS. 23 and 24.

When $\Delta P < ds$, (case a), the image of the function g(x) is reversed with respect to the image of g(x) obtained when $\Delta P > ds$, (case b). This result may be employed to detect small variations in periodicity, $P_A$, about an expected value $P_E$.

The difference between actual and expected periodicity, $\Delta P$ can be determined by counting the number of reconstructed periods displayed. In the aliased imaging technique of the present invention, one complete period of the image is reconstructed from a number of samples, $N_A(\Delta P)$, calculated as follows:

$$N_A(\Delta P) = \frac{P_A}{(ds - \Delta P)} = \frac{(P_E - \Delta P)}{(ds - \Delta P)}$$

where again, $P_A$ is the actual periodicity of the target function, $P_E$ is the expected periodicity and $\Delta P = P_A - P_E$. The number of periods, $N_P$, of the target function that are displayed is given by:

$$N_P = \frac{N_S}{N_A(\Delta P)}$$

where $N_S$ is the total number of samples acquired by the beam in one sweep across a dimension of the specimen.

The ratio of the number of periods, $N_P$, that are displayed, to the number of periods expected is given by:

$$\xi(\Delta P) = \frac{N_P(\Delta P)}{N_P(0)}$$
$$= \frac{N_A(0)}{N_A(\Delta P)}$$
$$= \frac{\frac{P_E}{ds}(ds - \Delta P)}{(P_E - \Delta P)}$$

To simplify this expression, we define the following two dimensionless variables:

$$\gamma = ds/P_E$$

$$\beta = \Delta P/P_E$$

Then, we have:

$$\xi(\Delta P) = \frac{(\gamma - \beta)}{\gamma(1 - \beta)}$$

Solving this equation for $\beta$ yields:

$$\beta(\Delta P) = \frac{\gamma[\xi(\Delta P) - 1]}{[\gamma\xi(\Delta P) - 1]}.$$

Suppose, for a specimen exhibiting the sine-squared intensity distribution, f, given above, with an expected periodicity of $P_E=1$ μm, that the chosen sampling pitch is $ds'=P_E+ds=1.1$ μm. Then the expected image, corresponding to $\beta(0)=0$, is that shown in FIG. 25. The number of periods of the target function in one dimension that are expected to be displayed is:

$$N_P^E = \frac{ds}{P_E}N_S = \gamma N_s = 0.1 \times (256) = 25.6$$

where the superscript, E, denotes that this is the number of displayed periods that are expected. This corresponds well with the number of periods that are obtained from counting the periods in one dimension shown in FIG. 25.

Figure 25:
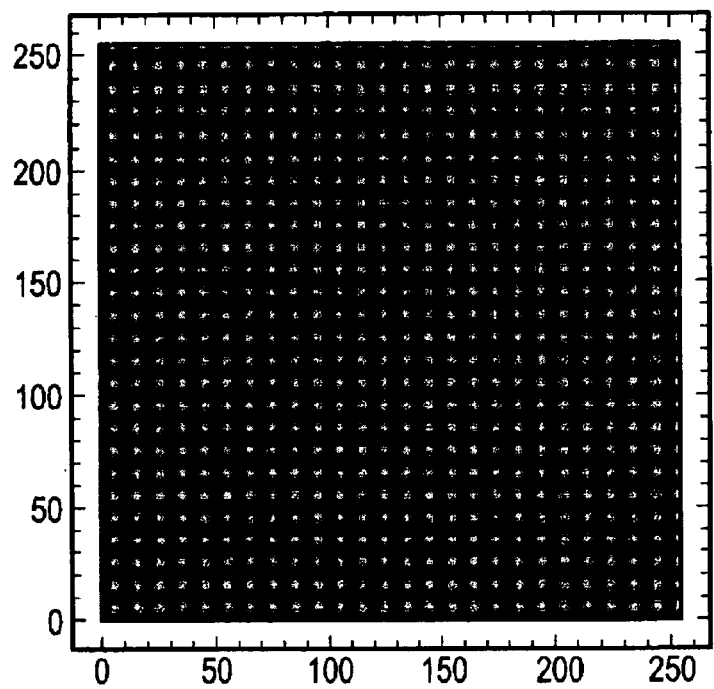
FIG. 25 shows aliased image sampling of a two-dimensional periodic spatial response function with a sampling pitch of ds'=P+P/10 and $\Delta$P/P=0 in each direction.
Figure 26:
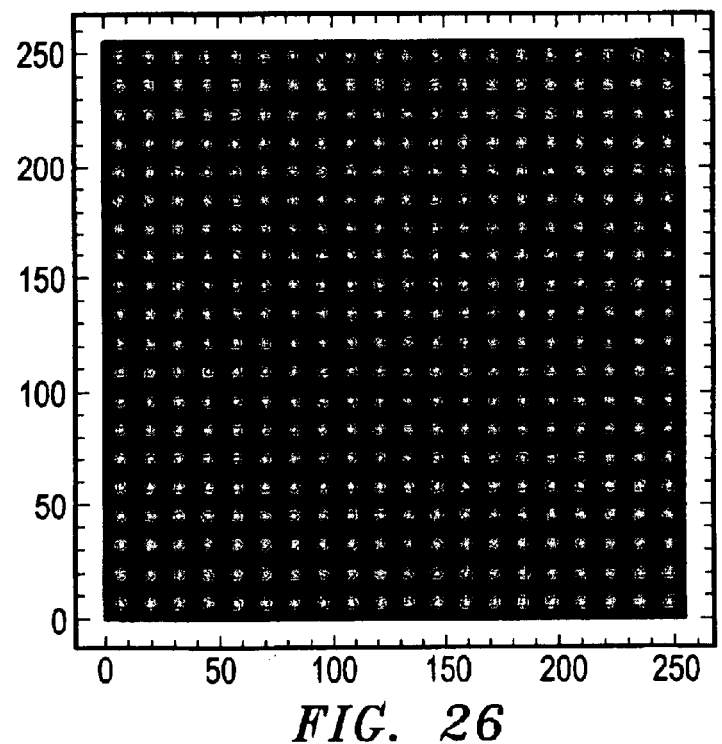
FIG. 26 shows aliased image sampling of a two-dimensional periodic spatial response function with a sampling pitch of ds'=P+P/10 and $\Delta$P/P=1/50 in each direction.
Figure 27:
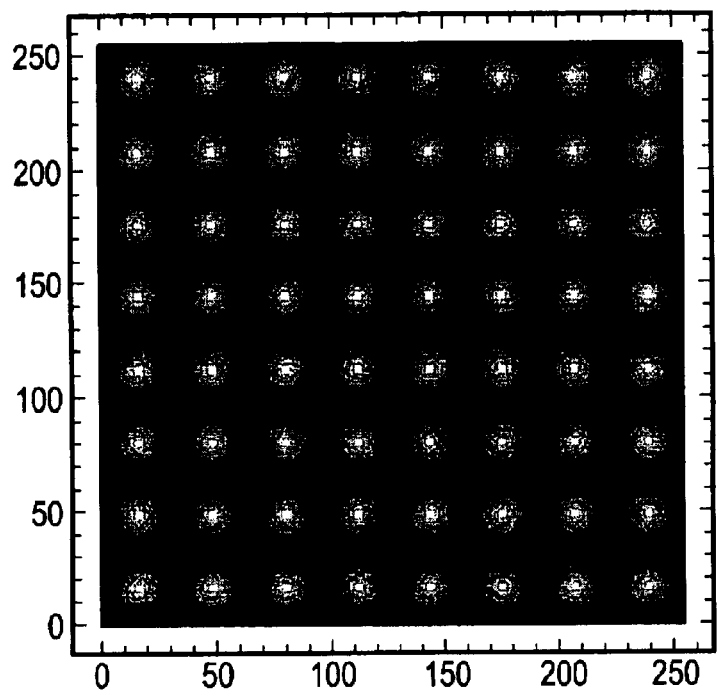
FIG. 27 shows aliased image sampling of a two-dimensional periodic spatial response function with a sampling pitch of ds'=P+P/10 and $\Delta$P/P=1/15 in each direction.
Figure 28:
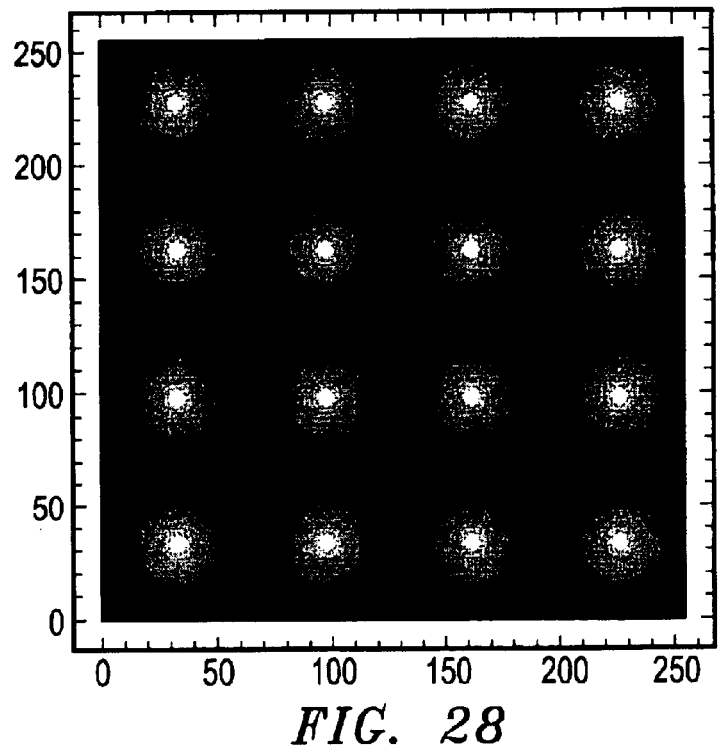
FIG. 28 shows aliased image sampling of a two-dimensional periodic spatial response function with a sampling pitch of ds'=P+P/10 and $\Delta$P/P=1/12 in each direction.
Figure 29:
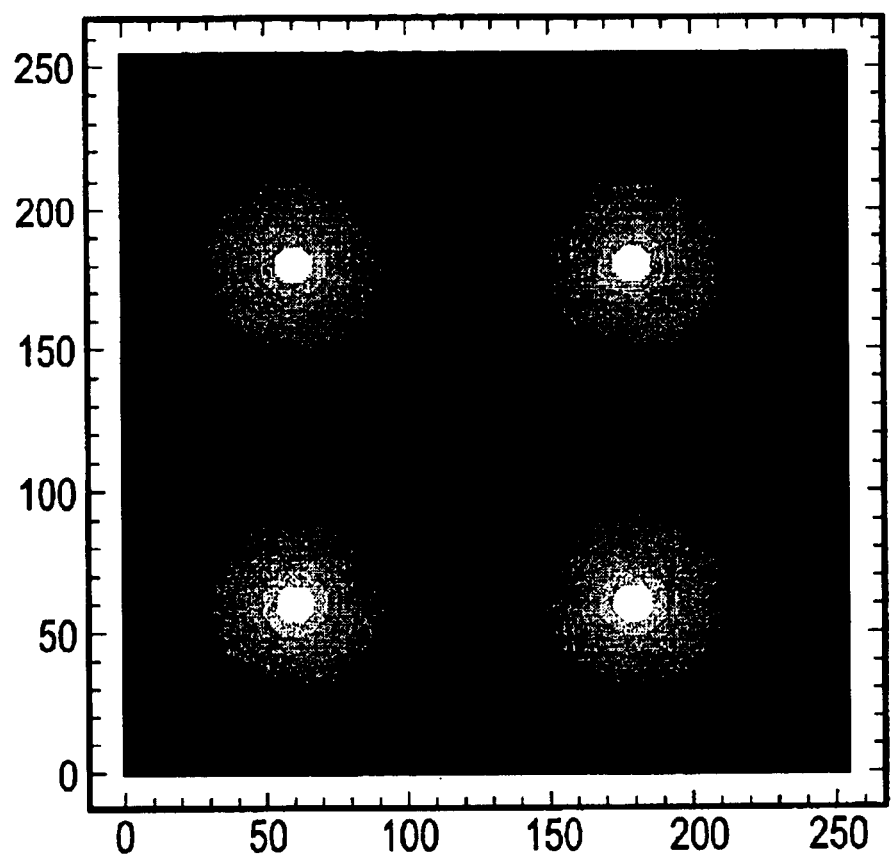
FIG. 29 shows aliased image sampling of a two-dimensional periodic spatial response function with a sampling pitch of ds'=P+P/10 and $\Delta$P/P=1/11 in each direction.

Suppose that instead of receiving the expected image of FIG. 25, corresponding to $P_E=1$ μm, we obtain the image shown in FIG. 26. The unknown periodicity of this function is $P_A=1.02$. We can obtain successively more accurate approximations to $P_A$ as follows: An approximate count of the number of periods displayed in FIG. 26 in one dimension results in $N_P^O(\Delta P)=20$, where the superscript, O, denotes that this is the number of periods actually observed. The ratio of the number of periods observed to the number of periods expected gives an approximation, $\xi^O(\Delta P)$, to $\xi(\Delta P)$:

$$\xi^O(\Delta P) = \frac{N_P^O}{N_P^E} = \frac{20}{25.6} = 0.781$$

From this we can obtain an approximation, $\beta^O(\Delta P)$, to the actual value of $\beta(\Delta P)$:

$$\beta^O(\Delta P) = \frac{\gamma(\xi^O - 1)}{(\gamma\xi^O - 1)} = 0.023$$

which leads to the approximation, $P^O$, to the actual value of $P_A$ as follows:

$$P^O = P_E\beta^O + P_E = 1.023 \, \mu m$$

The error in this approximation is 0.003 μm or less than 3% of the actual periodicity, $P_A$.

Now, if the current approximation, $P^O$, is used as the expected periodicity and the image is re-sampled with the same pitch of ds=0.1, a new approximation to $\xi(\Delta P)$ can be obtained by again counting the number of displayed periods. From this, a closer approximation to the actual periodicity, $P_A$, can be obtained. This process can be repeated until the approximate value, $\beta^O(\Delta P)$, becomes arbitrarily small, or equivalently, until the approximate value, $\xi^O(\Delta P)$, becomes arbitrarily close to one. Thus, the aliased imaging technique can be employed to determine with high accuracy the periodicity of a reference sample. This reference sample can be used to achieve high accuracy in beam calibration. Note that this process can be performed by manually or automatically according to a suitable algorithm employing pattern recognition techniques.

FIGS. 25, 26, 27, 28, and 29 illustrate the display of images derived for $\beta=0$, $\beta=0.02$, $\beta=0.066$, $\beta=0.083$, and $\beta=0.091$ respectively. By counting the periods displayed in the images and approximating $\beta$ according to the method described above we obtain the following approximations, $\beta^O$, and the resulting percentages of error between the exact and approximated values of $\beta$.

| β | $\xi^O$ | $\beta^O$ | Error |
|---|---|---|---|
| 0.02 | 0.781 | 0.023 | 15% |
| 0.066 | 0.313 | 0.071 | 6% |
| 0.083 | 0.156 | 0.086 | 3% |
| 0.091 | 0.078 | 0.093 | 2% |

Observe, that as $\beta$ approaches ds, the error decreases to zero, as would be expected.

The method of aliased image scanning can also be advantageously employed to detect rotational misalignment between the axes of the periodic specimen pattern and the axes of the scan field. Consider once again the periodic specimen represented by the periodic function $f(x, y, P)$ defined above. Once again, equal periodicity in the x and y directions is assumed for clarity. Suppose there exists a rotational misalignment of an angle θ between the specimen axes and the scan field axes. Then the coordinates of the specimen, denoted (X, Y) are related to the scan field coordinates, (x, y), through the following relationships:

$$X(x,y,\theta) = x\cos(\theta) - y\sin(\theta)$$

$$Y(x,y,\theta) = x\sin(\theta) + y\cos(\theta)$$

Figure 30:
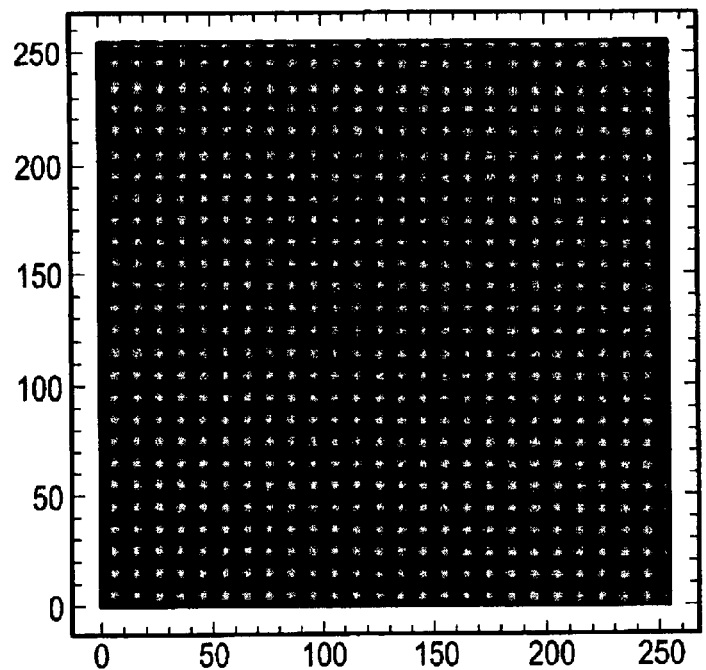
FIG. 30 shows conventional sampling of a two-dimensional periodic spatial response function with a sampling pitch of ds=P/10 in each direction: the axes of the function are rotated with respect to the scan axes by an angle of 0.5 degrees.

For illustration, suppose that P=1 μm and θ=0.5 degrees. When this specimen is sampled according to the conventional method with a sampling pitch of ds=0.1 μm, the image shown in FIG. 30 is produced. Note that the small angular rotation of the specimen is scarcely discernable, rendering precise rotational alignment highly difficult.

Figure 31:
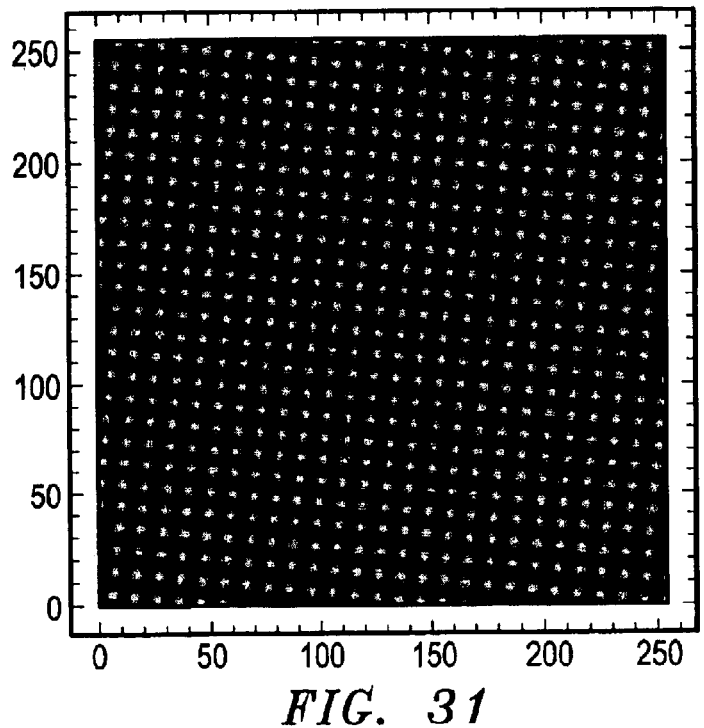
FIG. 31 shows aliased image sampling of a two-dimensional periodic spatial response function with a sampling pitch of ds'=P+P/10 in each direction: the axes of the function are rotated with respect to the scan axes by an angle of 0.5 degrees.

Now consider the same specimen sampled according to the method of the present invention with a sampling pitch of ds'=P+ds=1.1 μm. Recall that for this value of ds' the resultant image would be the same as if the specimen were sampled conventionally with a sampling pitch of ds, provided that θ is equal to zero. However, with a small angular rotation of 0.5 degrees between the axes of the specimen and the scan field axis, the image shown in FIG. 31 is obtained. Comparison of FIGS. 30 and 31 show that aliased image scanning produces a very pronounced increase in the apparent angular rotation of the specimen. The apparent angular rotation, θ', is related to the actual angular rotation as follows:

$$\frac{\sin(\theta')}{\sin(\theta)} = \frac{ds'}{ds}$$

For small angles this formula simplifies to:

$$\frac{\theta'}{\theta} = \frac{ds'}{ds}$$

Since ds' is much greater than ds, θ is much greater than θ. Thus, the angular rotation will be much more pronounced when aliased image scanning is employed. The expected numerical value of θ for the present example is 5.5 degrees, which corresponds well with the rotation observed in FIG. 31.

Although the magnification of rotational misalignment is pronounced when aliased image scanning is employed, the scale and periodicity of the aliased image appear unchanged. In fact, these quantities are reduced by a factor of cos(θ'), which is approximately one for small values of θ'.

The apparent angle of rotation created by aliased image scanning can be magnified further by increasing ds'. When θ=0, aliased image scanning with a pitch of ds'=nP+ds produces identical images for all integer values, n. However, when θ is not zero, the apparent rotation scales by a factor of n according to the relation:

$$\sin(\theta') = \sin(\theta)\frac{nP + ds}{ds}$$

which, for small angles and small values of ds, simplifies to:

$$\theta' = \frac{nP\theta}{ds}$$

Figure 32:
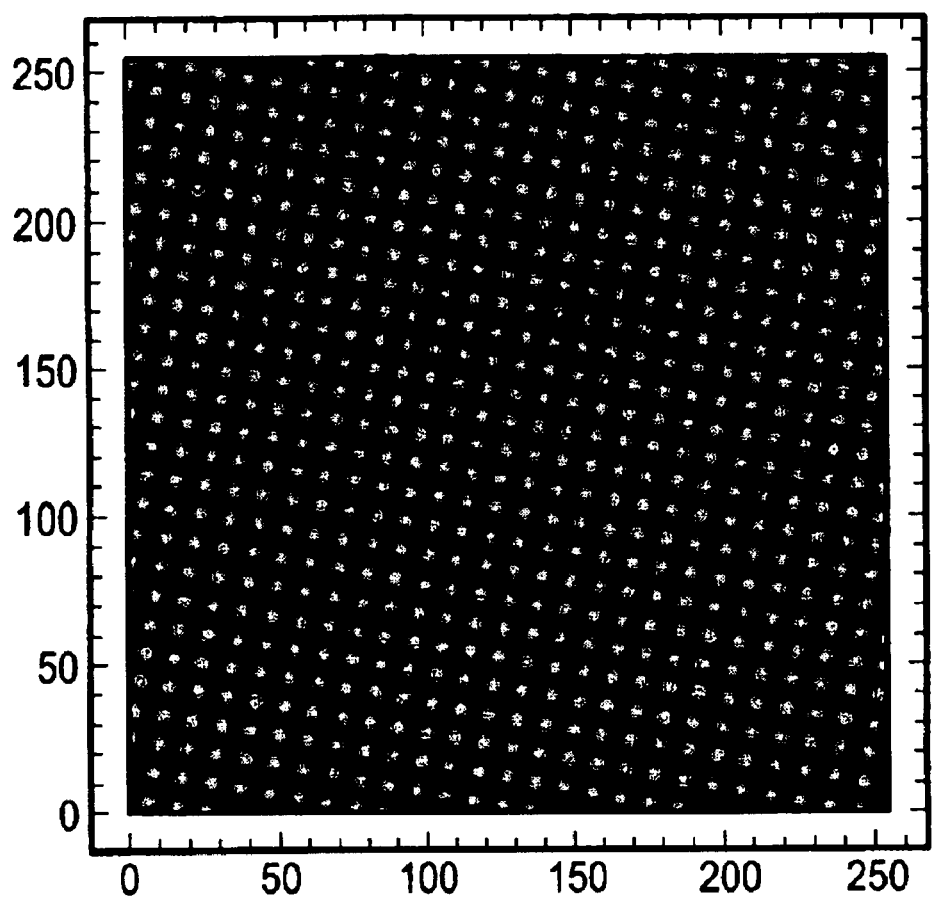
FIG. 32 shows aliased image sampling of a two-dimensional periodic spatial response function with a sampling pitch of ds'=2P+P/10 in each direction: the axes of the function are rotated with respect to the scan axes by an angle of 0.5 degrees.

Suppose that n is increased to two, while the other parameters of the example above are kept constant: θ=0.5, P=1 μm, and ds=0.1 μm. The resultant image is shown in FIG. 32. The apparent angular rotation is sufficiently pronounced to measure θ' directly from the image to be about 10 degrees. From this measurement, we can calculate θ:

$$\theta = \theta'\frac{ds}{nP} = 0.5 \text{ degrees}$$

Figure 33:
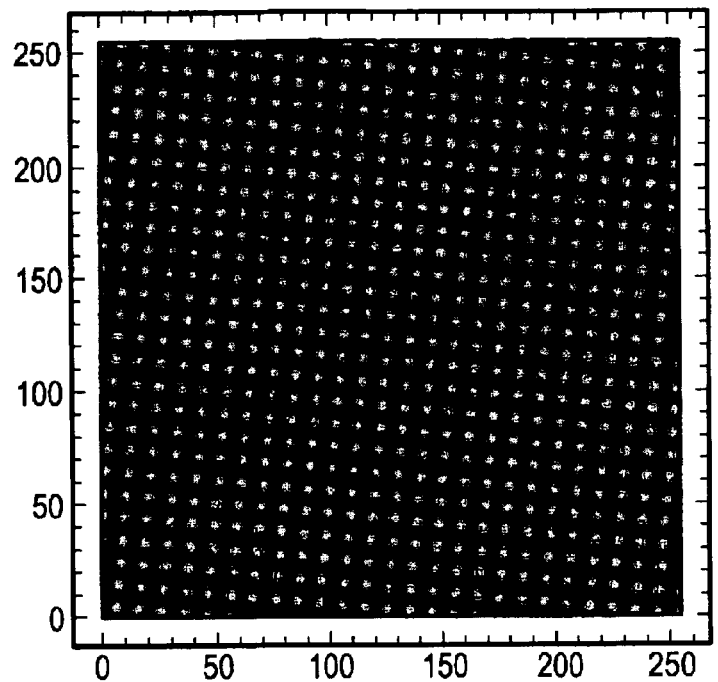
FIG. 33 shows aliased image sampling of a two-dimensional periodic spatial response function with a sampling pitch of ds'=1.1 $\mu$m in each direction: the axes of the function are rotated with respect to the scan axes by an angle of 0.5 degrees.
Figure 34:
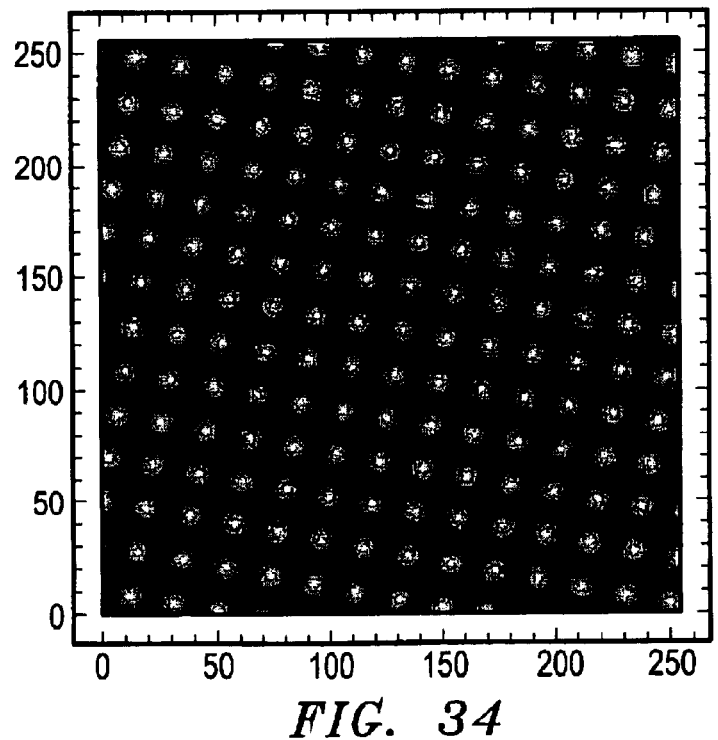
FIG. 34 shows aliased image sampling of a two-dimensional periodic spatial response function with a sampling pitch of ds'=1.05 $\mu$m in each direction: the axes of the function are rotated with respect to the scan axes by an angle of 0.5 degrees.
Figure 35:
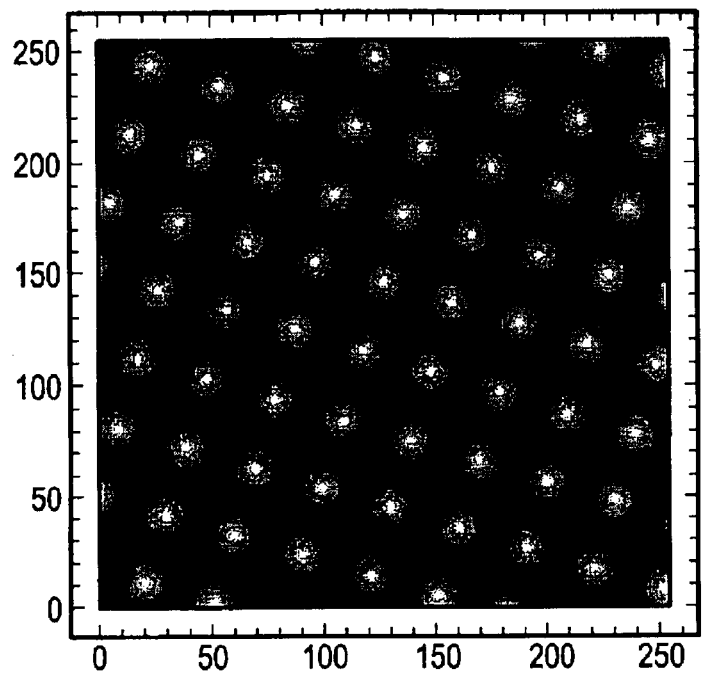
FIG. 35 shows aliased image sampling of a two-dimensional periodic spatial response function with a sampling pitch of ds'=1.03 $\mu$m in each direction: the axes of the function are rotated with respect to the scan axes by an angle of 0.5 degrees.
Figure 36:
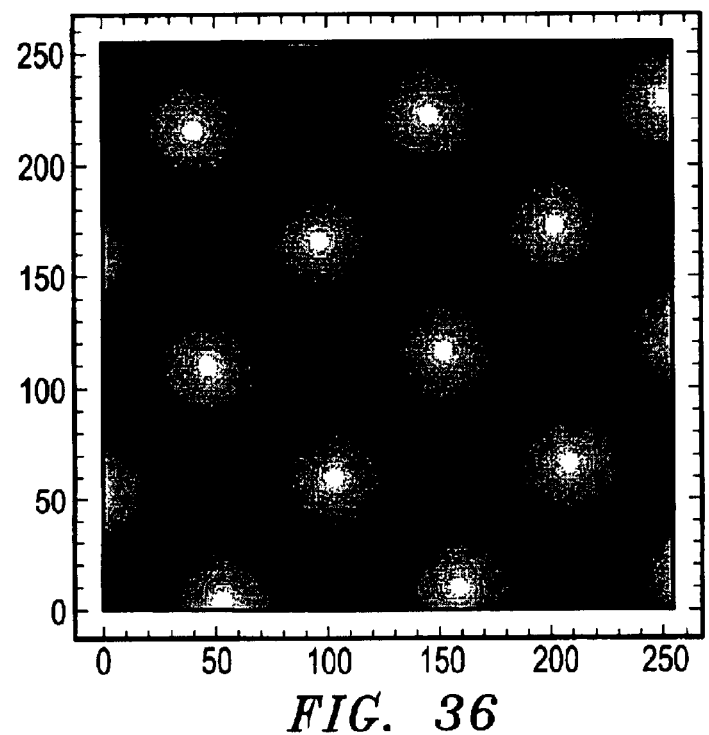
FIG. 36 shows aliased image sampling of a two-dimensional periodic spatial response function with a sampling pitch of ds'=1.01 $\mu$m in each direction: the axes of the function are rotated with respect to the scan axes by an angle of 0.5 degrees.
Figure 37:
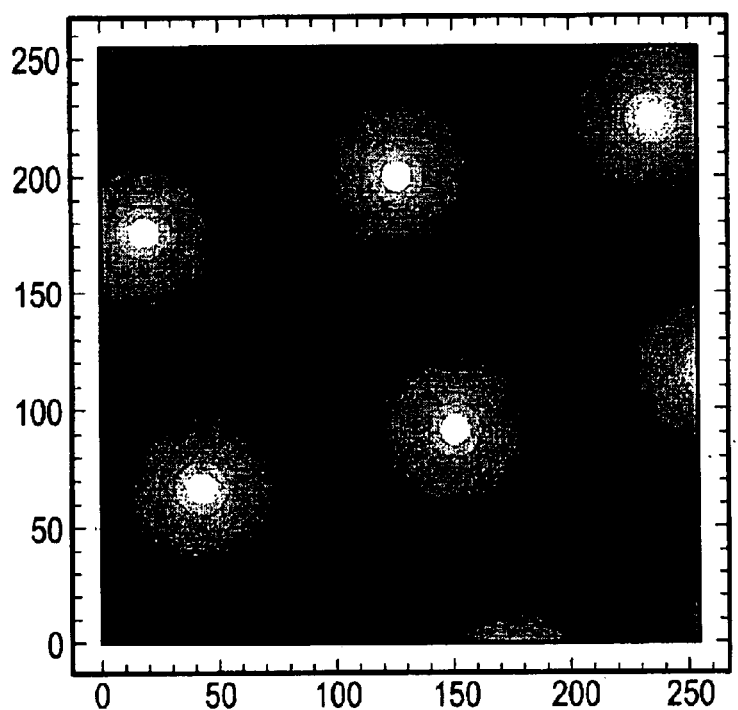
FIG. 37 shows aliased image sampling of a two-dimensional periodic spatial response function with a sampling pitch of ds'=1.002 $\mu$m in each direction: the axes of the function are rotated with respect to the scan axes by an angle of 0.5 degrees.
Figure 38:
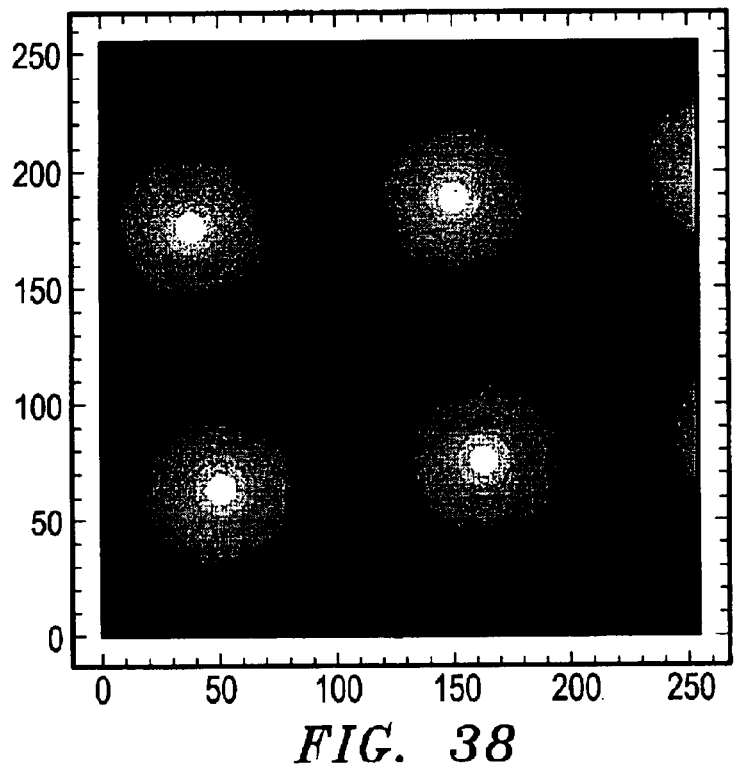
FIG. 38 shows aliased image sampling of a two-dimensional periodic spatial response function with a sampling pitch of ds'=1.001 $\mu$m in each direction: the axes of the function are rotated with respect to the scan axes by an angle of 0.5 degrees.
Figure 39:
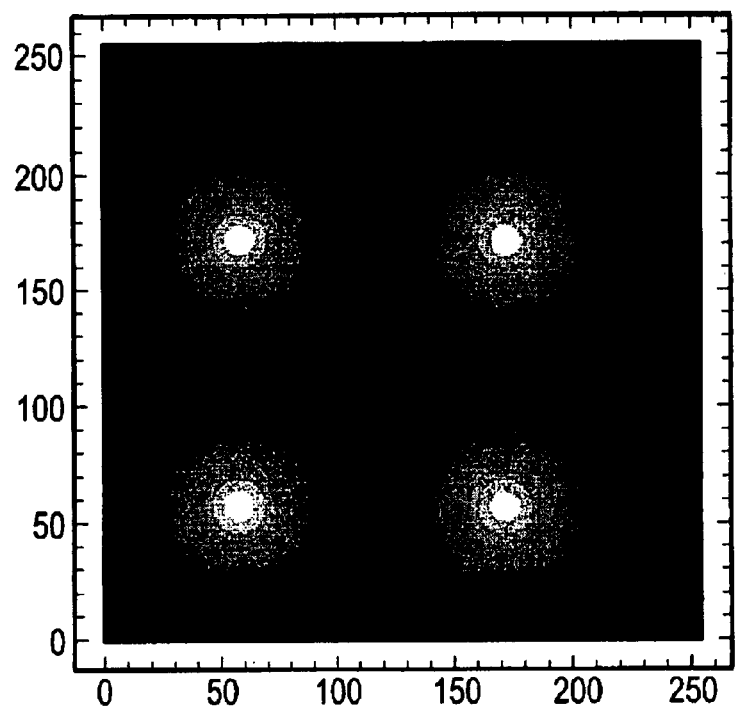
FIG. 39 shows aliased image sampling of a two-dimensional periodic spatial response function with a sampling pitch of ds'=1.0 $\mu$m in each direction: the axes of the function are rotated with respect to the scan axes by an angle of 0.5 degrees.
Figure 40:
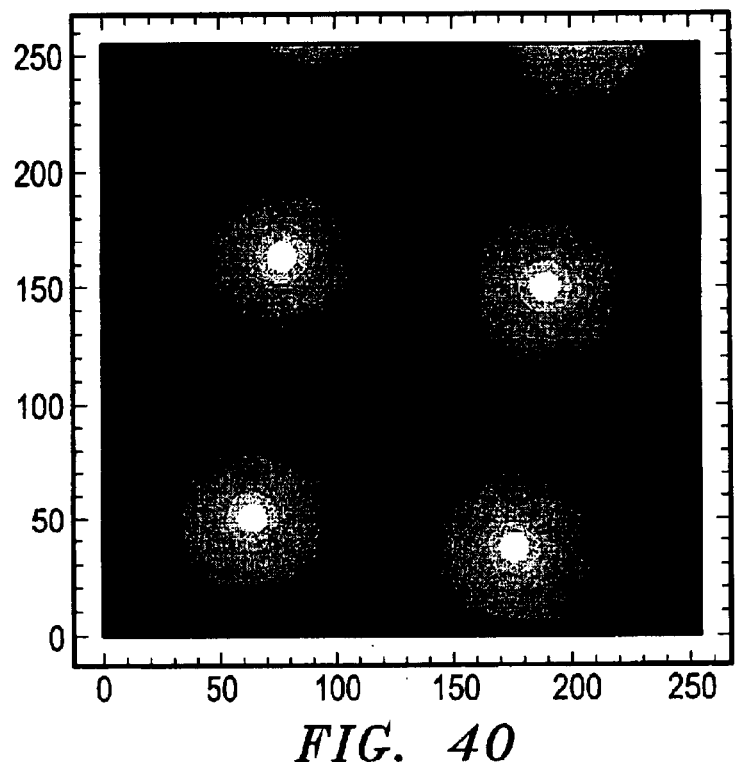
FIG. 40 shows aliased image sampling of a two-dimensional periodic spatial response function with a sampling pitch of ds'=0.999 $\mu$m in each direction: the axes of the function are rotated with respect to the scan axes by an angle of 0.5 degrees.
Figure 41:
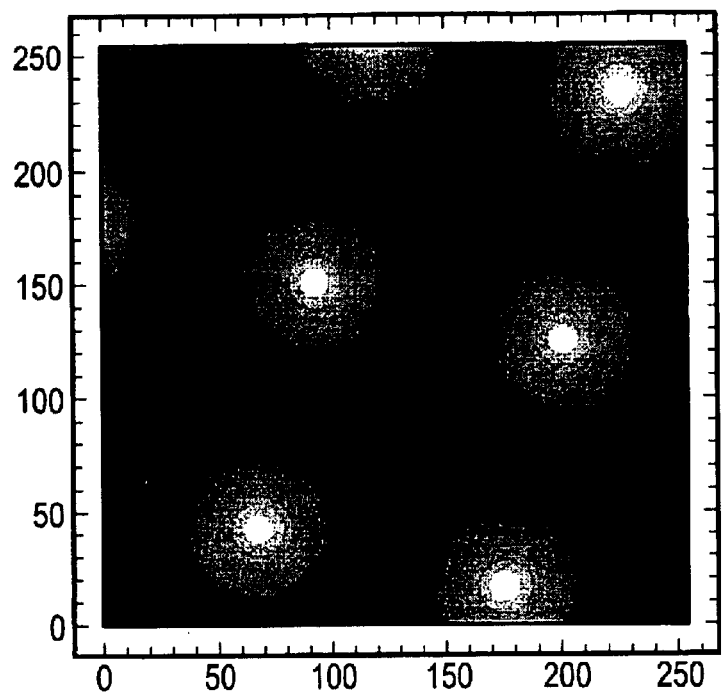
FIG. 41 shows aliased image sampling of a two-dimensional periodic spatial response function with a sampling pitch of ds'=0.998 $\mu$m in each direction: the axes of the function are rotated with respect to the scan axes by an angle of 0.5 degrees.
Figure 42:
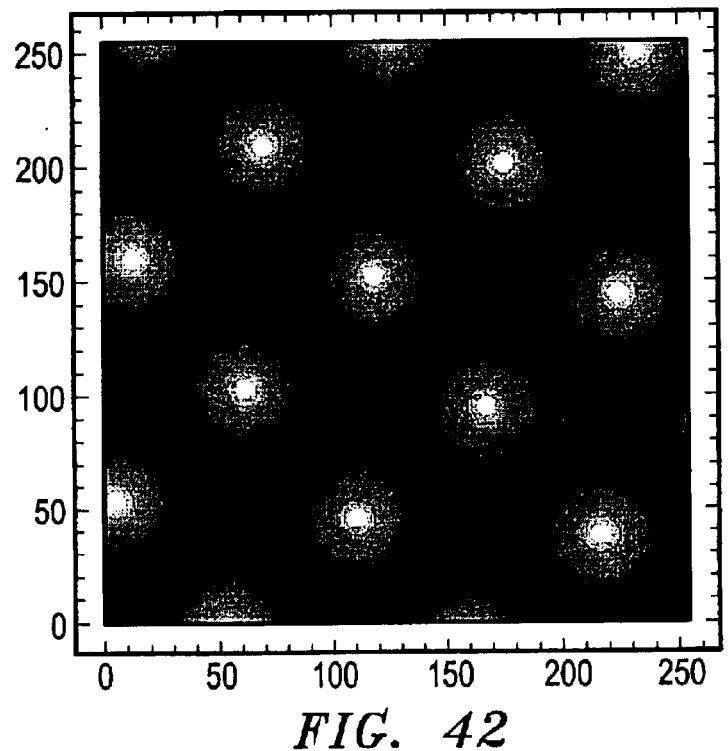
FIG. 42 shows aliased image sampling of a two-dimensional periodic spatial response function with a sampling pitch of ds'=0.99 $\mu$m in each direction: the axes of the function are rotated with respect to the scan axes by an angle of 0.5 degrees.
Figure 43:
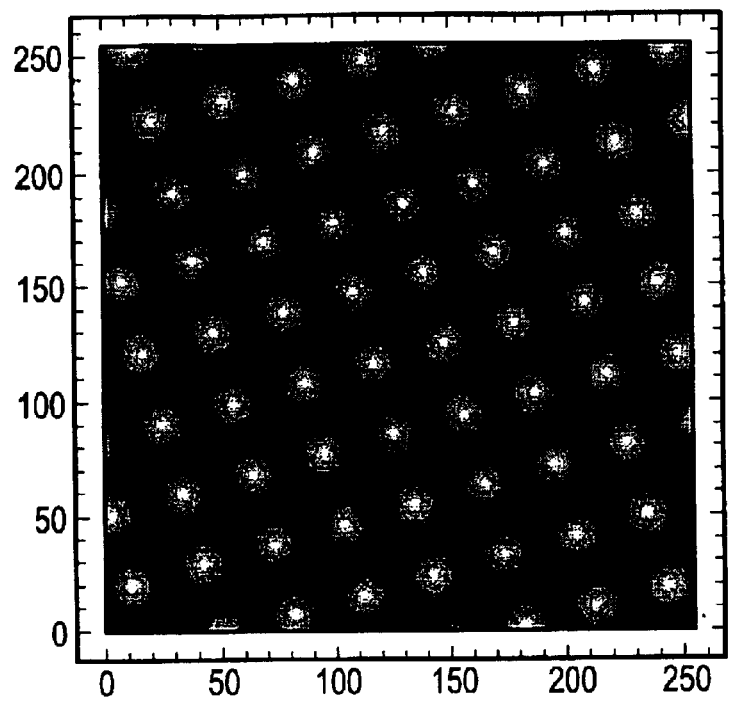
FIG. 43 shows aliased image sampling of a two-dimensional periodic spatial response function with a sampling pitch of ds'=0.97 $\mu$m in each direction: the axes of the function are rotated with respect to the scan axes by an angle of 0.5 degrees.
Figure 44:
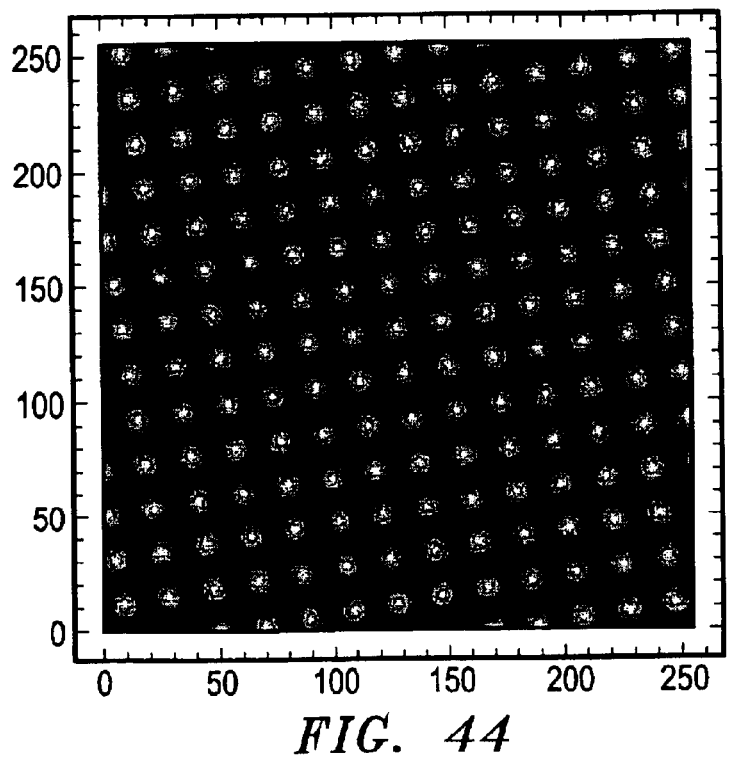
FIG. 44 shows aliased image sampling of a two-dimensional periodic spatial response function with a sampling pitch of ds'=0.95 $\mu$m in each direction: the axes of the function are rotated with respect to the scan axes by an angle of 0.5 degrees.
Figure 45:
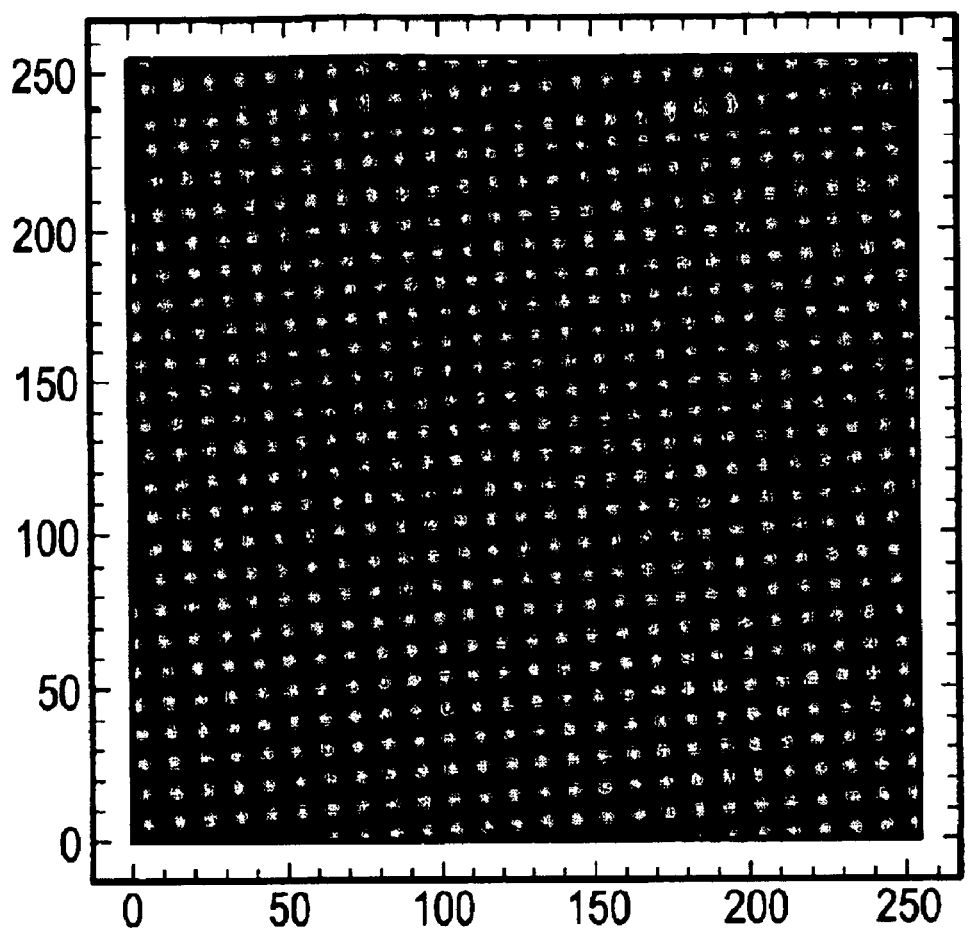
FIG. 45 shows aliased image sampling of a two-dimensional periodic spatial response function with a sampling pitch of ds'=0.90 $\mu$m in each direction: the axes of the function are rotated with respect to the scan axes by an angle of 0.5 degrees.

Now consider the effect upon the image of varying the sample pitch value, ds'=P+ds, by small increments of the value of ds. With an angular rotation of the specimen of θ=0.5 degrees and with P=1 μm we let ds=0.1 and obtain the image of FIG. 33. With ds=0.5 we obtain the image of FIG. 34. Note that as ds is decreased the displayed image undergoes an angular rotation as well as a magnification of scale.

The affect of changing ds is shown in FIGS. 33 through 45 for corresponding to the following table of values of ds:

| FIG. No. | ds | ds' |
|---|---|---|
| 33 | 0.1 | P + 0.1 |
| 34 | 0.05 | P + 0.05 |
| 35 | 0.03 | P + 0.03 |
| 36 | 0.01 | P + 0.01 |
| 37 | 0.002 | P + 0.002 |
| 38 | 0.001 | P + 0.001 |
| 39 | 0.00 | P |
| 40 | −0.001 | P − 0.001 |
| 41 | −0.002 | P − 0.002 |
| 42 | −0.01 | P − 0.01 |
| 43 | −0.03 | P − 0.03 |
| 44 | −0.05 | P − 0.05 |
| 45 | −0.1 | P − 0.1 |

Notice that as ds decreases toward zero, the rotation of the image increases toward 90 degrees as the image magnification increases. As ds continues to decrease toward −0.1, the rotation of the image increases toward 180 degrees as the magnification decreases. Note further, that when a small angle of rotation, θ, is introduced between the specimen and the scan field axes, the condition of maximum magnification, ds'=P, does not result in a constant gray level display as would be expected when θ is equal to zero.

The phenomenon just described can be used to detect whether the periodicity of a given specimen matches a reference periodicity. That is, by rotating the specimen by a small fixed angle with respect to the scan field axes and then successively adjusting ds', the condition of maximum magnification and 90 degrees of rotation occurs when ds'=P. In this way the periodicity of the specimen can be determined with high precision.

The present invention can also be advantageously employed to detect and correct for non-orthogonal conditions arising from non-orthogonality of the target pattern of the specimen, or non-orthogonality of the scan beam, or both. A non-orthogonal condition can be expressed in terms of a deviation angle, α, between an axis of the specimen and an axis of the scan field as follows:

$X(x,y,\alpha) = x\cos(\alpha) - y\sin(\alpha)$ $Y(x,y,\alpha) = y$

For example, suppose that the periodicity of the specimen is P=1 μm and the deviation angle, α, is 0.5 degrees. Conventional scanning with a sample pitch of ds=0.1 μm produces the image shown in FIG. 6. A small non-orthogonal condition is observable upon close examination of the image. The difficulty of observation of this error makes compensation for orthogonal conditions difficult.

Figure 46:
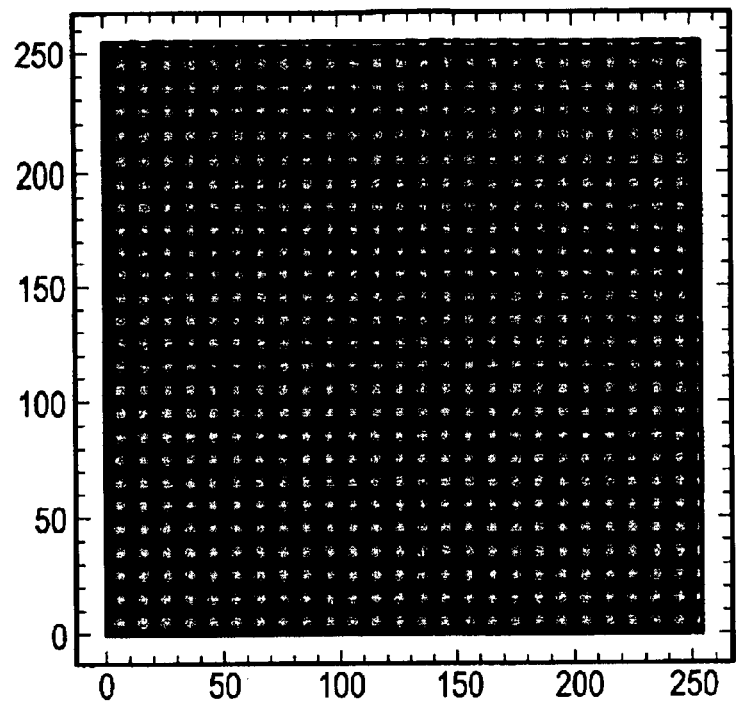
FIG. 46 shows conventional sampling of a two-dimensional periodic spatial response function with a sample pitch of ds=P/10: the x-axis of the function is rotated with respect to the x-axis of the scan by an angle of 0.5 degrees.
Figure 47:
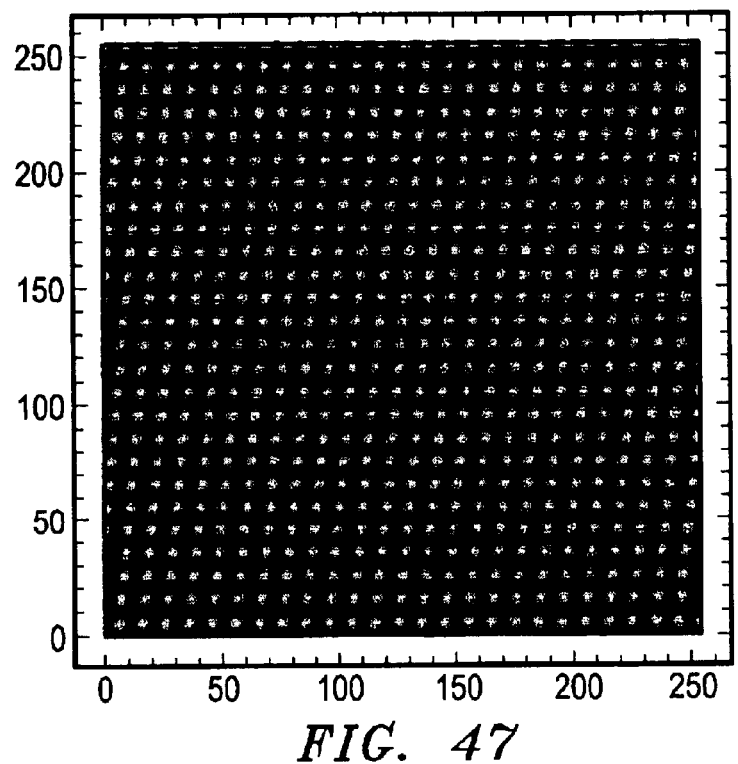
FIG. 47 shows aliased image sampling of a two-dimensional periodic spatial response function with a sample pitch of ds'=P+P/10: the x-axis of the function is rotated with respect to the x-axis of the scan by an angle of 0.5 degrees.
Figure 48:
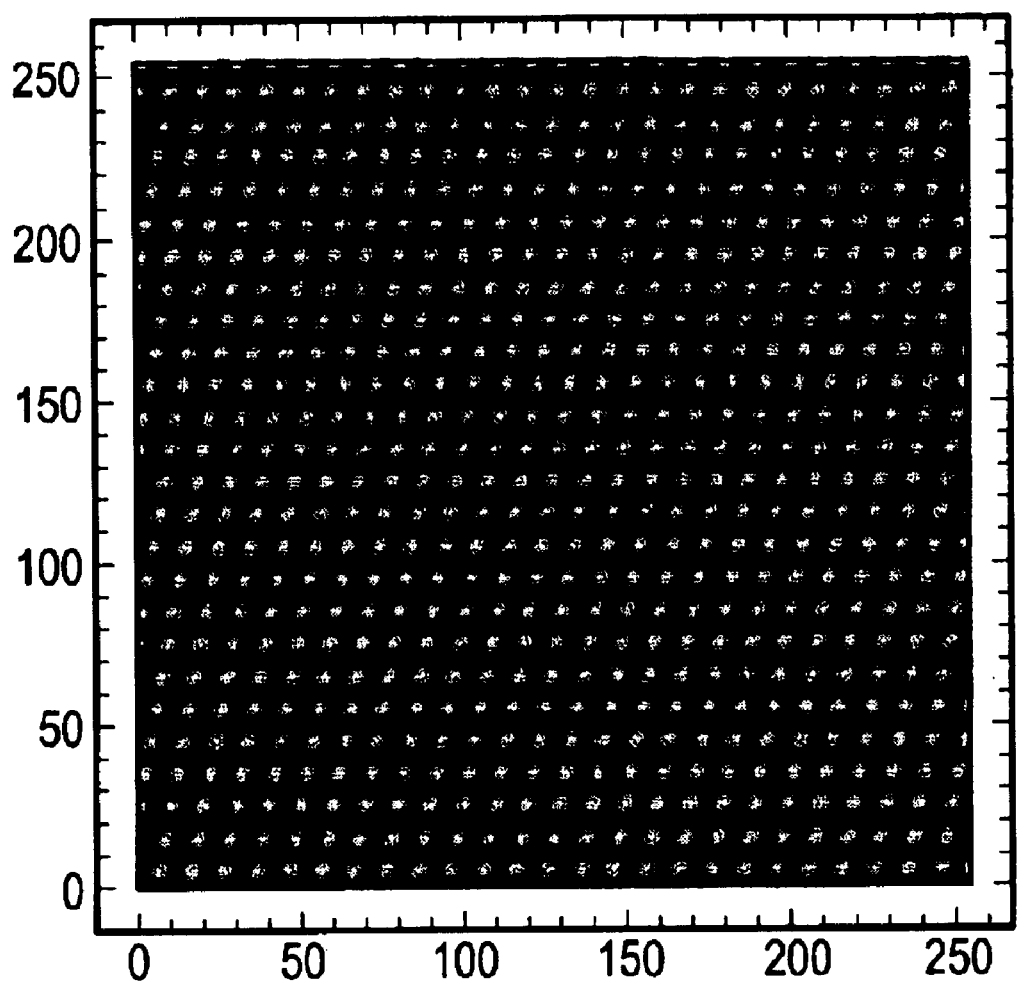
FIG. 48 shows aliased image sampling of a two-dimensional periodic spatial response function with a sample pitch of ds'=2P+P/10: the x-axis of the function is rotated with respect to the x-axis of the scan by an angle of 0.5 degrees.

Now consider the same conditions except that the specimen is scanned according to the methods of the present invention with ds'=P+ds=1.1 μm. The resultant image is shown in FIG. 47. Clearly, the non-orthogonal condition is much more pronounced in comparison to FIG. 46. If ds' is increased to ds'=2P+ds=2.1 μm, the effect is even more pronounced, as shown in FIG. 48. Thus, the present invention enables a much more precise calibration of the scan beam to eliminate non-orthogonal conditions.

The present invention may also be advantageously employed to detect and correct for anisotropic conditions arising from differences in scale factors in the x and y directions, whether arising from the condition of the specimen or lack of correct beam calibration. Suppose that a relative stretch of the x-axis by a factor, κ, exists:

$X = x/\kappa$ $Y = y$

Figure 49:
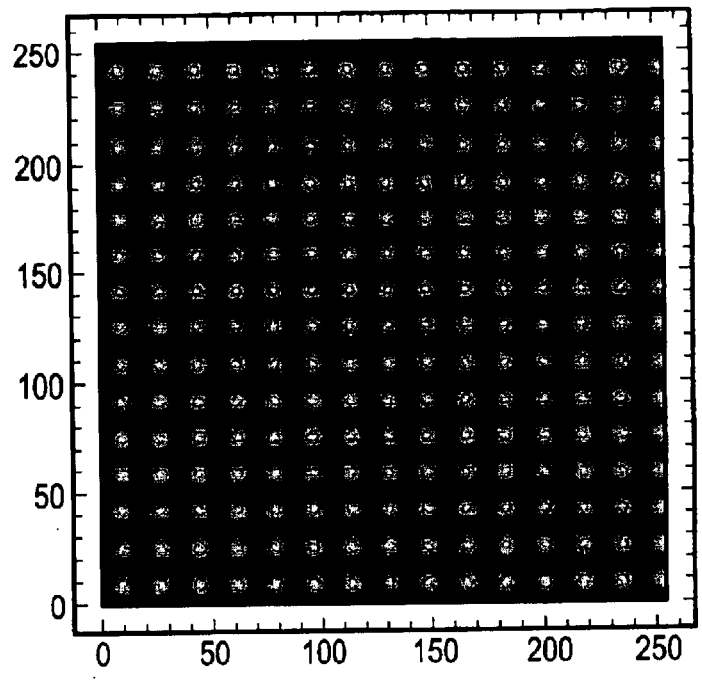
FIG. 49 shows conventional sampling of a two-dimensional periodic spatial response function with a sampling pitch of ds=0.06 $\mu$m: the x-axis of the function is scaled with respect to the x-axis of the scan by a factor of 1.05.
Figure 50:
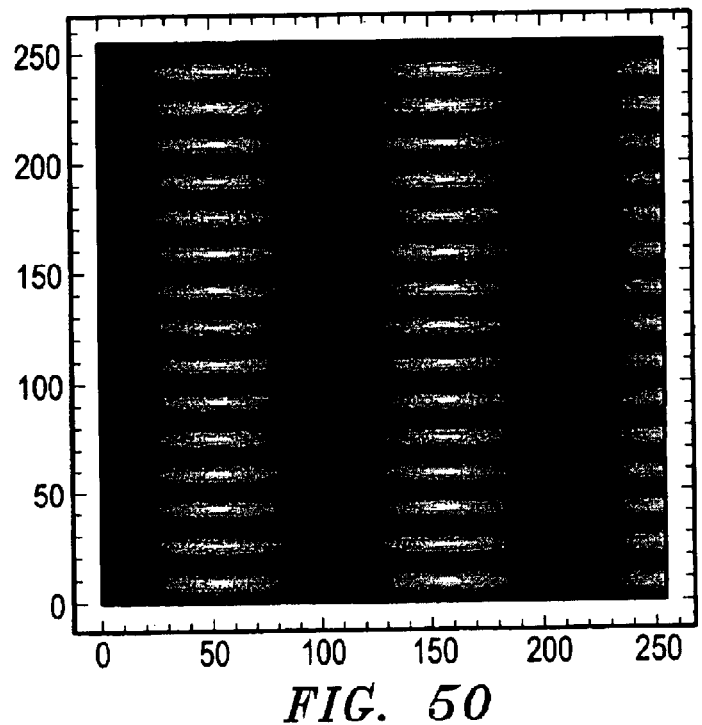
FIG. 50 shows aliased image sampling of a two-dimensional periodic spatial response function with a sampling pitch of ds'=P+0.06 $\mu$m: the x-axis of the function is scaled with respect to the x-axis of the scan by a factor of 1.05.

For example, suppose $\kappa=1.05$ and $P=1$ μm. Conventional sampling with pitch ds=0.06 results in the image shown in FIG. 49. Aliased image scanning with pitch ds'=P+ds=1.06 μm results in the image shown in FIG. 50. Clearly, the pronounced effect obtained by aliased image scanning enables detection and correction of even very small anisotropic conditions.

Thus, the method of aliased image scanning may be employed to achieve very fine calibration because of error magnification, enabling the operator to calibrate for changes in working height, irregularities in scan gain, non-orthogonal conditions, rotational misalignment, beam focus eccentricities and other aberrant conditions.

Therefore, the methods of the present invention are well suited for scanned beam system calibration. In conventional imaging, the sampling pitch must be very small compared to the target features to be resolved. This restriction is removed without loss of resolution in aliased image scanning where a sample pitch greater than the periodicity of the targets in an array is used. The resulting increase between successive beam positions minimizes the area dose per image scan. This leads to reduced target damage, allowing for longer dwell times, an increase in the number of acquisition frames, and higher beam currents. In addition, aliased image scanning increases the observability of misalignment, scaling, and rotation errors, which allows for calibration of the scanned beam system with much higher precision. The large magnification of errors achieved by the present invention also makes the aliased image scanning techniques particularly suitable for automated calibration of the system operating under the direction of software.

Note that the rectangular array of sampling points and targets shown in the figures is but one embodiment for implementing the present invention. Other sampling patterns and target patterns may be used, so long as the relative positions of each sample point and target location are defined so that an image of the shape may be constructed from points on each of the target samples. Formation of the image shape may be performed continually by repeatedly sampling the array of targets and displaying the samples obtained by each complete scan of the specimen. This allows the operator to make adjustments while visualizing the effect of his or her adjustments. Since the samples taken during a complete scan of the calibration specimen according to the methods of the present invention are widely spaced, the large particle dosages that are destructive of the surface to be imaged does not occur. Moreover, with suitable processing, the positions of each sample within each target can be different for each different complete scan of the calibration specimen so that the same point within a target is not sampled more than once in any set of complete scans of the array. Also note that although the targets are preferably of substantially identical size and shape this is not especially critical for large arrays of small targets.

Note further that an aliased image calibration specimen comprising an array of targets for calibration of a scanned beam system as described above may be etched or deposited on a wafer during the process of etching or deposition of integrated circuitry structure on the wafer. In this way, a calibration specimen is automatically provided with each wafer submitted for subsequent scanned beam processing. This allows for focusing and calibration without loading a separate calibration specimen and then replacing it with the wafer to be deposited or etched.

Thus, the methods of the present invention described above assist the operator of a scanned beam system to achieve highly accurate beam focus, stigmation correction and rotational alignment. Further, the methods may be employed to increase the accuracy and reliability of algorithms designed to achieve automated beam focus, automated stigmation correction and automated rotational alignment, and other aberrant effects.

Although the present invention and its advantages have been described in detail, it should be understood that various changes, substitutions and alterations can be made herein without departing from the spirit and scope of the invention as defined by the appended claims. The invention achieves multiple objectives, such as reducing calibration specimen damage and improving calibration sensitivity. Because the invention can be used in different applications for different purposes, not every embodiment falling within the scope of the attached claims will achieve every objective. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for calibration of a scanned beam system, comprising the steps of:
   sampling a specimen comprising an array of targets with a spacing between samples that is greater than a spacing between targets in the array; and
   obtaining information from the samples concerning calibration of the system.

2. The method of claim 1, wherein the step of obtaining information from the samples further comprises the step of determining an extent to which a focal point of a beam deviates from an expected point.

3. The method of claim 1, wherein the step of obtaining information from the samples further comprises the step of determining an extent to which a position of the specimen deviates from an expected position.

4. The method of claim 1, wherein the step of obtaining information from the image further comprises the step of determining an extent to which a target periodicity deviates from an expected target periodicity.

5. The method of claim 1, wherein the step of obtaining information from the samples further comprises the step of determining an extent of rotational misalignment of the specimen.

6. The method of claim 1, wherein the step of obtaining information from the samples further comprises the step of determining an extent of rotational misalignment of deflection axes of the beam.

7. The method of claim 1, wherein the step of obtaining information from the samples further comprises the step of determining a periodicity of the targets.

8. The method of claim 1, wherein the step of obtaining information from the samples further comprises the stop of determining an extent of beans non-orthogonality.

9. The method of claim 1, wherein the step of obtaining information from the samples further comprises the step of determining an extent of non-orthogonality of a pattern of the targets.

10. The method of claim 1, wherein the step of obtaining information from the samples further comprises the step of determining an extent of beam anisotropy.

11. The method of claim 1, wherein the stop of obtaining information from the samples further comprises the step of determining an extent of anisotropy of a pattern of the targets.

12. The method of claim 1, wherein the array of targets is a rectangular array.

13. The method of claim 1, wherein the spacing between samples is uniform along a dimension of the array.

14. The method of claim 1, wherein the step of obtaining information from the samples further comprises the step of observing an image formed from the samples.

15. The method of claim 1, wherein the spacing between samples is adjusted iteratively to obtain information concerning calibration of the system.

16. The method of claim 1, wherein the specimen further comprises integrated circuitry.

17. The method of claim 1, further comprising the step of employing information concerning calibration of the system to evaluate an automated beam calibration system.

18. A scanned beam calibration system comprising:
a specimen comprising an array of targets;
a beam deflection subsystem adapted to sample the specimen with a spacing between samples that is greater than a spacing between targets in the array; and
a subsystem adapted to provide information derived from the samples concerning calibration of the system.

19. The system of claim 18, wherein the subsystem adapted to provide information from the samples comprises an imaging device adapted to form an image from the samples.

20. The system of claim 18, wherein the subsystem adapted to provide information from the samples comprises processing circuitry conditioned to process data obtained from the samples.

21. The system of claim 18, wherein the subsystem adapted to provide information from the samples comprises a process for determining an extent to which a focal point of a beam deviates from an expected point.

22. The system of claim 18, wherein the subsystem adapted to provide information from the samples comprises a process for determining an extent to which a target periodicity deviates from an expected target periodicity.

23. The system of claim 18, wherein time subsystem adapted to provide information from the samples comprises a process for determining an extent to which a position of the specimen deviates from arm expected position.

24. The system of claim 18, wherein the subsystem adapted to provide information from the samples comprises a process for determining an extent of rotational misalignment of the specimen with respect to deflection axes of the beam.

25. The system of claim 18, wherein the subsystem adapted to provide information from the samples comprises a process for determining wherein the step of obtaining information from the samples further comprises the step of determining an extent of beam non-orthogonality.

26. The system of claim 18, wherein the subsystem adapted to provide information from the samples comprises a process for determining an extent of non-orthogonality of a pattern of the targets.

27. The system of claim 18, wherein the subsystem adapted to provide information from the samples comprises a process for determining an extent of beam anisotropy.

28. The system of claim 18, wherein the subsystem adapted to provide information from the samples comprises a process for determining an extent of anisotropy of a pattern or the targets.

29. The system of claim 18, wherein the spacing between samples is adjusted iteratively to achieve a refinement of calibration of the system.

30. The system of claim 18, wherein the system is automated according to an algorithm adapted to achieve calibration of the system.

31. The method of claim 1, wherein an expected position of a sample relative to an expected position of another sample is an integer multiple of an expected target spacing plus a constant that is less than the expected target spacing.

32. The method of claim 31, wherein the constant is small compared to the expected target spacing.

33. The method of claim 1, wherein the spacing between samples is less than twice the spacing between targets.

34. The method of claim 1, wherein a magnification resulting from a sample spacing that is greater than a spacing between targets is greater than a magnification resulting from a spacing of samples that is less than the spacing between targets.

35. The method of claim 1, wherein a system sensitivity resulting from a sample spacing that is greater than a spacing between targets is a function of the extent to which an actual target periodicity deviates from an expected periodicity.

36. The method of claim 35, wherein a target periodicity is determined from the obtained information.

37. The method of claim 1, wherein a system sensitivity resulting from a sample spacing that is greater than a spacing between targets is a function of the extent to which actual target positions within the array deviate from expected positions.

38. The method of claim 1, wherein a magnification of a rotational misalignment of the specimen is a function of the sample spacing.

39. The method of claim 1, wherein a magnification of a rotational misalignment of a beam sweep axis is a function of the sample spacing.

40. The method of claim 1, wherein a magnification of a scale factor of a sweep axis is a function of the sample spacing.

41. The method of claim 1, wherein a magnification of a non-orthogonality between beam sweep axes is a function of the sample spacing.

42. The method of claim 1, wherein a magnification of a non-orthogonality of a pattern of targets within the array is a function of the sample spacing.

43. The method of claim 1, further comprising the step of determining an extent to which target periodicity deviates front an expected value by rotating the specimen.

44. The method of claim 1, wherein a magnification of beam anisotropy is a function of the sample spacing.

45. The method of claim 1, wherein a magnification of an anisotropic pattern of targets within the array is a function of the sample spacing.

* * * * *